US008859059B2

(12) United States Patent
Naaman et al.

(10) Patent No.: US 8,859,059 B2
(45) Date of Patent: Oct. 14, 2014

(54) MAGNETIC PATTERNING METHOD AND SYSTEM

(75) Inventors: Ron Naaman, Yarkona (IL); Amos Bardea, Netanya (IL); Alexander Yoffe, Rehovot (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 333 days.

(21) Appl. No.: 13/127,358

(22) PCT Filed: Nov. 3, 2009

(86) PCT No.: PCT/IL2009/001026
§ 371 (c)(1),
(2), (4) Date: Jun. 16, 2011

(87) PCT Pub. No.: WO2010/061378
PCT Pub. Date: Jun. 3, 2010

(65) Prior Publication Data
US 2011/0236948 A1    Sep. 29, 2011

Related U.S. Application Data

(60) Provisional application No. 61/193,175, filed on Nov. 3, 2008, provisional application No. 61/171,873, filed on Apr. 23, 2009, provisional application No. 61/224,116, filed on Jul. 9, 2009.

(51) Int. Cl.
*B05D 1/32* (2006.01)

(52) U.S. Cl.
USPC .......................................................... 427/598

(58) Field of Classification Search
None
See application file for complete search history.

(56) References Cited

U.S. PATENT DOCUMENTS

| | | | | |
|---|---|---|---|---|
| 6,001,587 | A | * | 12/1999 | Turner et al. .................... 435/41 |
| 2004/0035942 | A1 | | 2/2004 | Silverman |
| 2004/0136494 | A1 | | 7/2004 | Lof et al. |
| 2008/0176109 | A1 | | 7/2008 | Kim et al. |

FOREIGN PATENT DOCUMENTS

| | | |
|---|---|---|
| JP | 2004 165665 | 6/2004 |
| JP | 2005 512761 A1 | 5/2005 |
| WO | WO 02/090002 A2 | 11/2002 |
| WO | WO 2005/065303 A2 | 7/2005 |
| WO | WO 2007/050035 A1 | 5/2007 |

OTHER PUBLICATIONS

Wilhelm et al., Langmuir, vol. 18, 2002, pp. 9485-9493.*
Kaufmann et al., Applied Materials Interfaces, vol. 1, No. 10, 2009, pp. 2320-2324, published on the web Sep. 24, 2009.*
Stewart et al.; "Unconventional methods for forming nanopatterns;" Proc. ImechE, *J. Nanoengineering and Nanosystems*; 2007; pp. 81-138; vol. 220.
Park et al.; "Highly crystalline anisotropic superstructures via magnetic field induced nanoparticle assembly," *Chem. Commun.*; 2007; pp. 5001-5003; The Royal Society of Chemistry.
Geissler et al.; "Microcontact-Printing Chemical Patterns with Flat Stamps;" *J. Am. Chem. Soc.*; 2000; pp. 6303-6304; vol. 122; American Chemical Society.
Quist et al.; "Recent advances in microcontact printing;" *Anal. Bioanal. Chem.*; 2005; pp. 591-600; vol. 381; Springer-Verlag.
Loo et al.; "Additive, nanoscale patterning of metal films with a stamp and a surface chemistry mediated transfer process: Applications in plastic electronics;" *Applied Physics Letters*; Jul. 15, 2002; pp. 562-564; vol. 81, No. 3, American Institute of Physics.
Jacobs et al.; "Submicrometer Patterning of Charge in Thin-Film Electrets;" *Science*; Mar. 2, 2001; pp. 1763-1766; vol. 291.
Michel et al.; "Printing meets lithography: Soft approaches to high-resolution printing;" *IBM J. Res. & Dev.*; Sep. 2001; pp. 697-719; vol. 45, No. 5.
Buxboim et al.; "A Single-Step Photolithographic Interface for Cell-Free Gene Expression and Active Biochips;" *Small*; 2007; pp. 500-510; vol. 3, No. 3; Wiley-VCH Verlag GmbH & Co., KGaA, Weinheim.
Hoff et al.; "Nanoscale Protein Patterning by Imprint Lithography;" *Nano Letters*; 2004; pp. 853-857; vol. 4, No. 5; American Chemical Society.
Urbach et al.; "Sub-100nm Confinement of Magnetic Nanoparticles Using Localized Magnetic Field Gradients;" *J. Am. Chem Soc.*, 2003; pp. 1 2704-12705; vol. 125; American Chemical Society.
Bandic et al.; "Magnetic Lithography Using Flexible Magnetic Masks: Applications to Servowriting;" *IEEE Transactions on Magnetics*; Sep. 2003; pp. 2231-2233; vol. 39, No. 5.

(Continued)

*Primary Examiner* — Allison Ford
*Assistant Examiner* — Yvonne Pyla
(74) *Attorney, Agent, or Firm* — Frommer Lawrence & Haug LLP; William S. Frommer

(57) ABSTRACT

The present invention relates to a method and apparatus for patterning a substrate. The method comprises providing at least one magnetic pattern generator configured and operable to modulate the magnetic field to induce varying magnetic properties to a magnetic field according to a desired pattern; applying the modulated magnetic field in the vicinity of the substrate creating a certain pattern of regions of interaction to be obtained on top of the substrate; and; interacting the substrate with magnetic particles, while under the application of the modulated magnetic field, the magnetic particles being attracted to selected regions of interaction defined by the certain pattern while being substantially not attracted to regions outside the regions of interaction, thus creating on top of the substrate the certain pattern of regions interacted with the magnetic particles. The desired pattern corresponds to a certain pattern for a predetermined magnetic field profile and at a predetermined distance from the magnetic pattern generator, where the sample is to be located.

24 Claims, 25 Drawing Sheets
(16 of 25 Drawing Sheet(s) Filed in Color)

(56) References Cited

OTHER PUBLICATIONS

McClelland et al.; "Nanoscale patterning of magnetic islands by imprint lithography using a flexible mold;" *Applied Physics Letters*; Aug. 19, 2002; pp. 1483-1485; vol. 81, No. 8; American Institute of Physics.

Pattani et al.; "Microcontact printing of quantum dot bioconjugate arrays for localized capture and detection of biomolecules;" *Biomed Microdevices*; 2008; pp. 367-374; vol. 10; Springer Science + Business Media, LLC.

Schmid et al.; "Preparation of Metallic Films on Elastomeric Stamps and Their Application for Contact Processing and Contact Printing;" *Advanced Functional Materials*; Feb. 2003; pp. 145-153; vol. 13, No. 2; Wiley-VCH Verlag GmbH & Co. KGaA, Weinheim.

Ino et al.; "Cell culture arrays using magnetic force-based cell patterning for dynamic single cell analysis;" *Lab on a Chip*; 2008; pp. 134-142; vol. 8; The Royal Society of Chemistry.

Shim at al.; "High Precision Fluidic Alignment of Carbon Nanotubes Using Magnetic Attraction on a Metal Catalyst;" *IEEE 21$^{st}$ International Conference on Micro Electro Mechanical Systems*; Jan. 13-17, 2008; pp. 729-732; Tucson, AZ, USA.

Bandic et al.; "Magnetic lithography for servowriting applications using flexible magnetic masks nanofabricated on plastic substrates;" *Microsyst. Technol.*; 2007; pp. 817-823; vol. 13; Springer-Verlag.

Hoeppener et al.; "Constructive Microlithography; Electrochemical Printing of Monolayer Template Patterns Extends Constructive Nanolithography to the Micrometer-Millimeter Dimension Range;" *Nano Letters*; 2003; pp. 761-767; vol. 3, No, 6; American Chemical Society.

\* cited by examiner

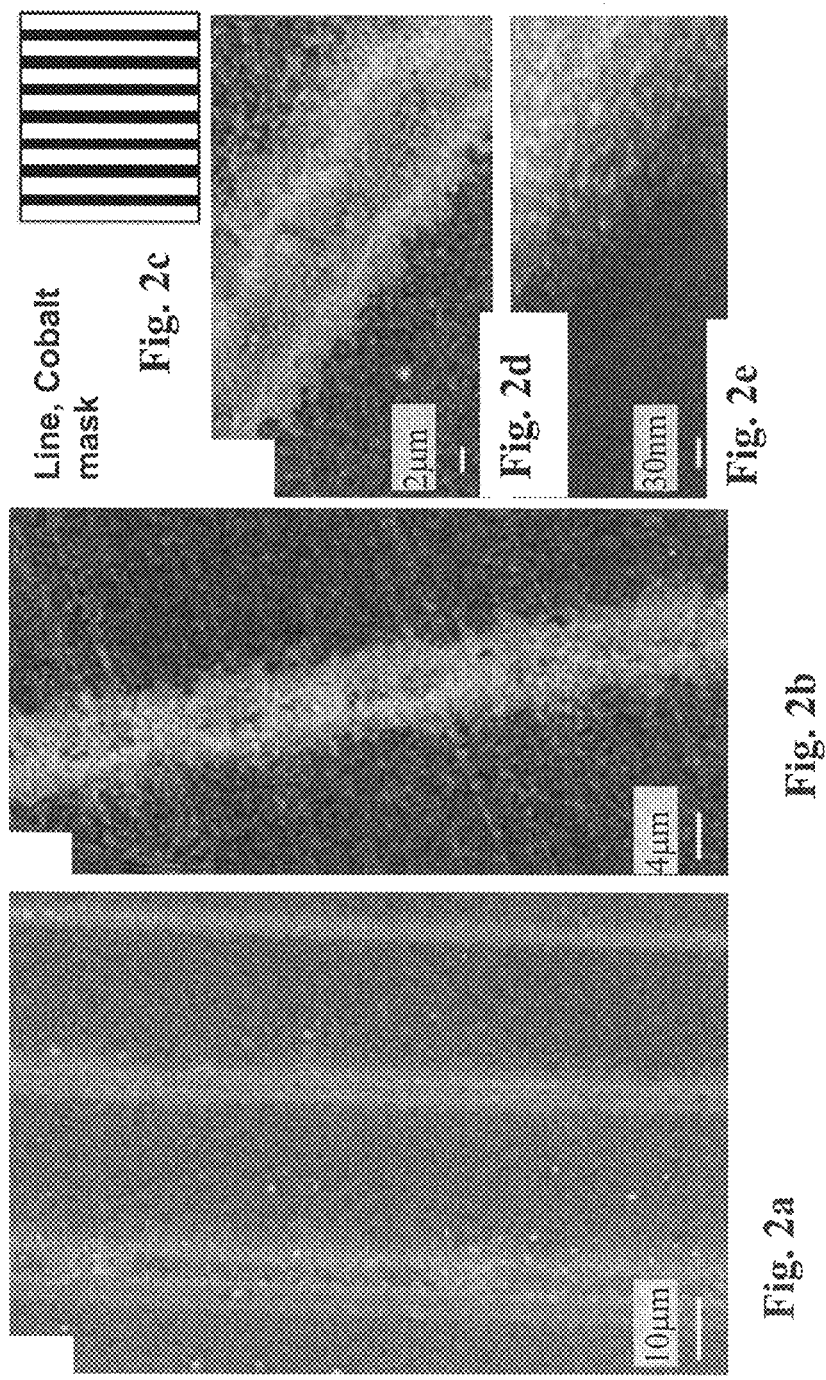

Grid, Cobalt mask

Fig. 4a
Fig. 4b
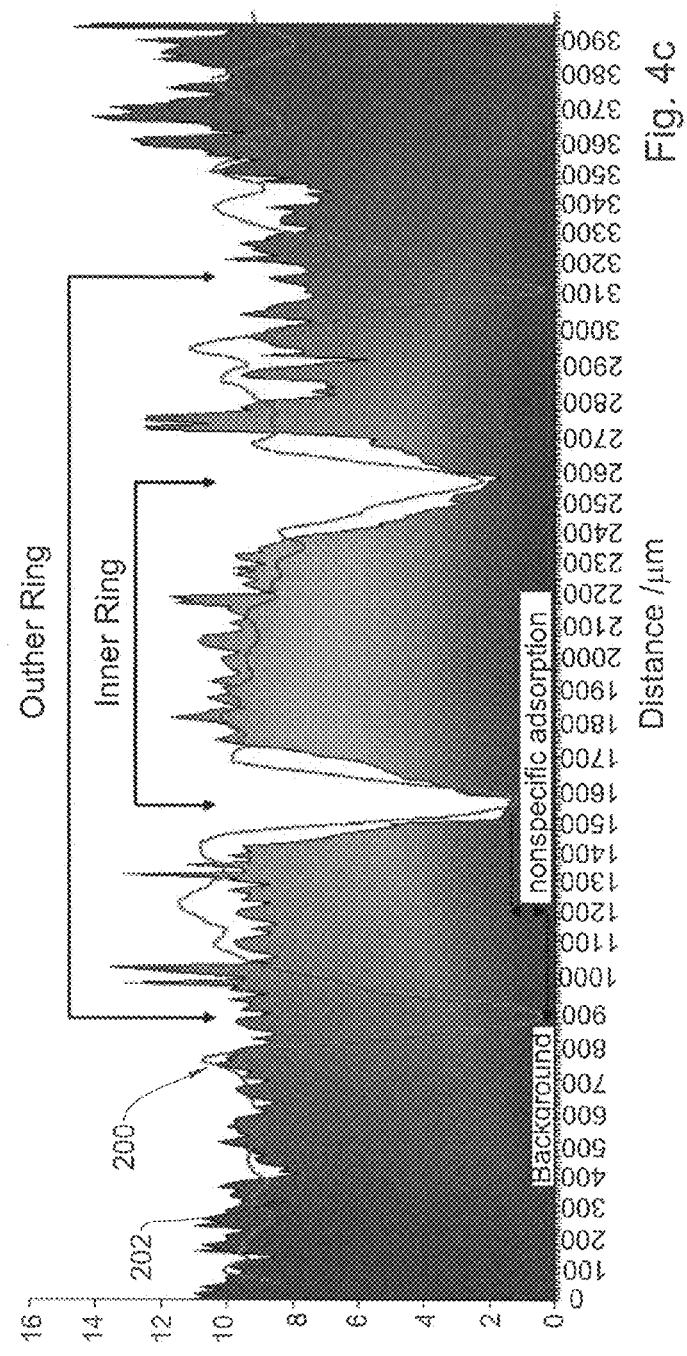
Fig. 4c

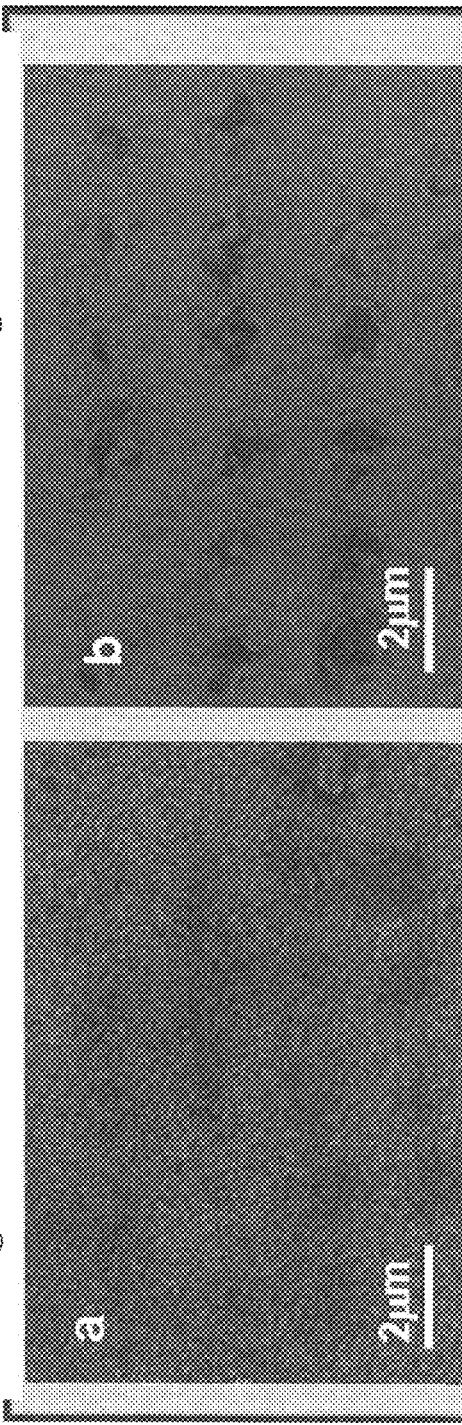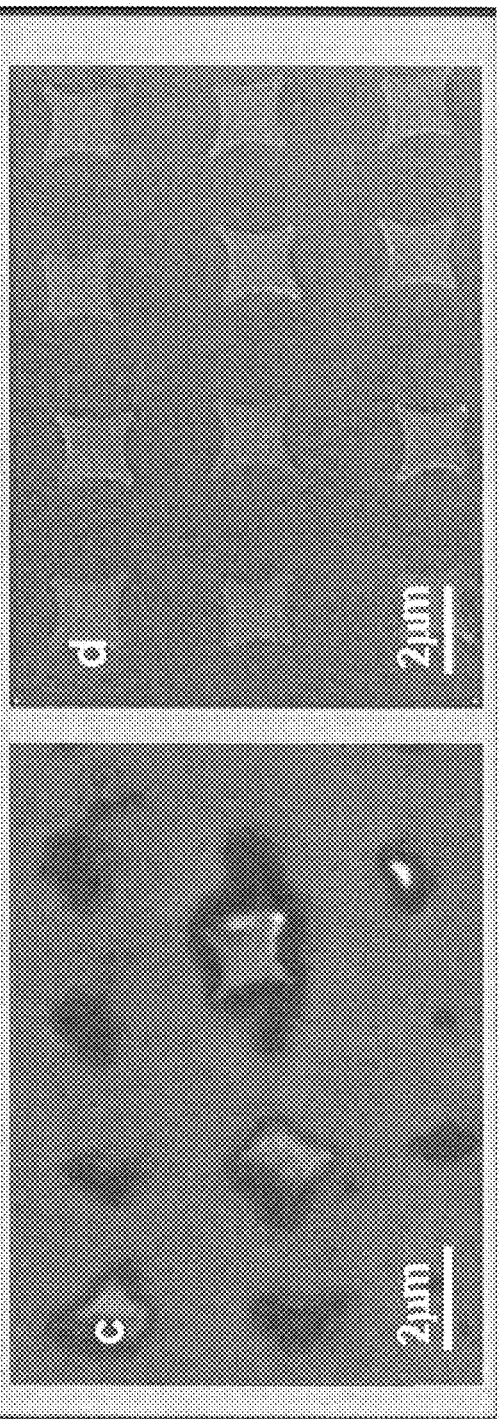

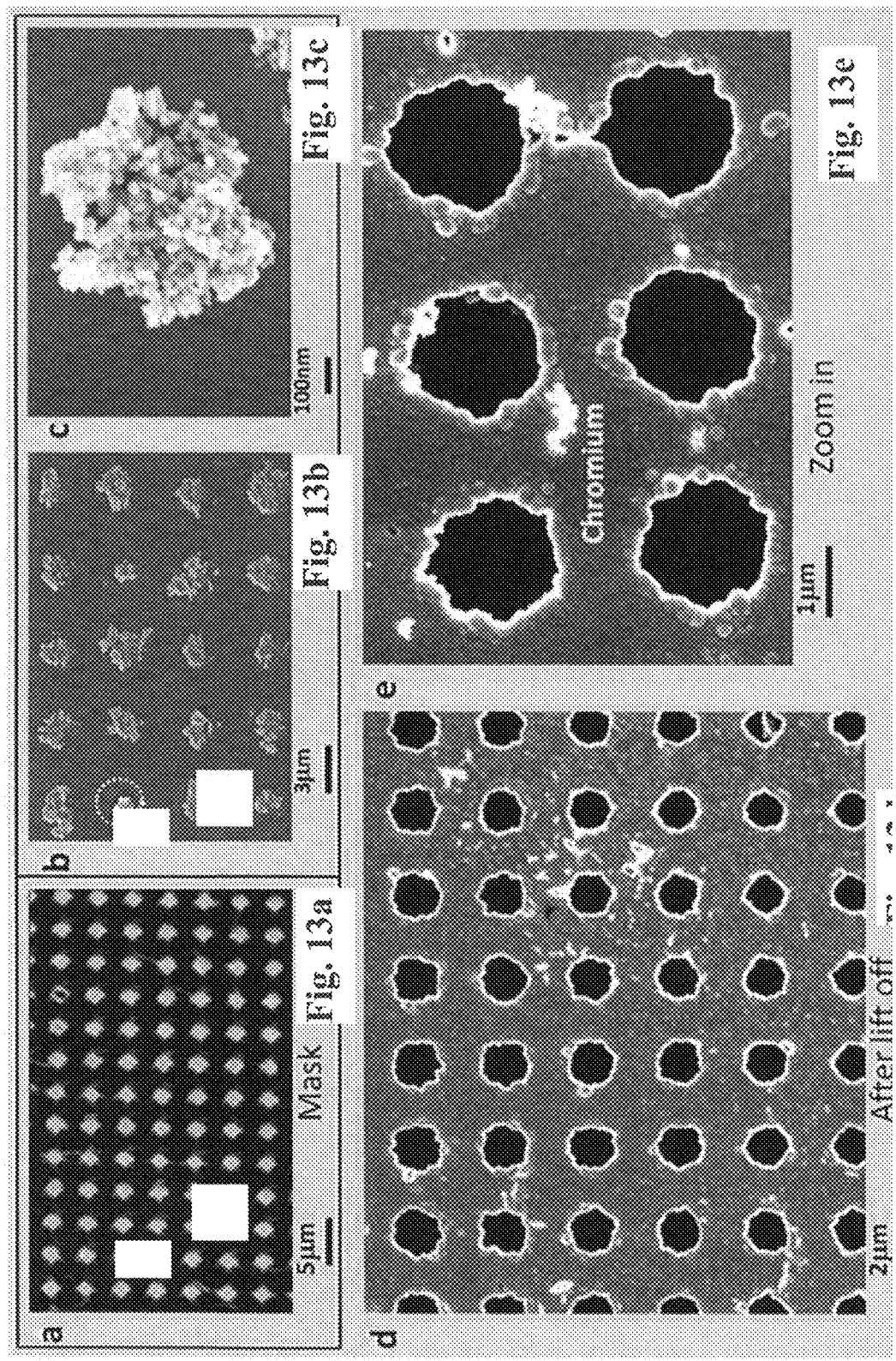

MAGNETIC PATTERNING METHOD AND SYSTEM

FIELD OF THE INVENTION

This invention is generally in the field of patterning techniques and relates to patterning using magnetic particles.

REFERENCES

The following references are considered to be pertinent for the purpose of understanding the background of the present invention:

1. Stewart, M. E., Motala, M. J., Yao, J., Thompson, L. B. & Nuzzo, R. G. Unconventional methods for forming nano-patterns. J. Nanoengineering and Nanosystems 220, 81-138 (2007).
2. Quist, A. P., Pavlovic, E. & Oscarsson, S. Recent advances in microcontact printing. Anal. Bioanal. Chem. 381, 591-600 (2005).
3. Park, J. I., Jun, Y. W., Choi, J. S. & Cheon, J. Highly crystalline anisotropic superstructures via magnetic field induced nanoparticle assembly. Chem. Commun. 5001-5003 (2007).
4. a) M. Geissler, A. Bernard, A. Bietsch, H. Schmid, B. Michel, E. Delamarche, Microcontact-printing chemical patterns with flat stamps J. Am. Chem. Soc. 2000, 122, 6303-6304; b) B. Michel, A. Bernard, A. Bietsch, E. Delamarche, M. Geissler, D. Juncker, H. Kind, J. P. Renault, H. Rothuizen, H. Schmid, P. Schmidt-Winkel, R. Stutz, H. Wolf, Printing meets lithography: Soft approaches to high-resolution patterning IBM J. Res. DeV. 2001, 45, 697-719.
5. Y. L. Loo, R. L. Willett, K. W. Baldwin, J. A. Rogers, Additive, nanoscale patterning of metal films with a stamp and a surface chemistry mediated transfer process: Applications in plastic electronics Appl. Phys. Lett. 2002, 81, 562-564
6. H. O. Jacobs, G. M. Whitesides, Submicrometer patterning of charge in thin-film electrets Science 2001, 291, 1763-1766
7. H. Schmid, H. Wolf, R. Allenspach, H Riel, S. Karg, B, Michel, Preparation of metallic films on elastomeric stamps and their application for contact processing and contact printing AdV. Fund. Mater. 2003, 13, 145-153
8. A. Buxboim, M. Bar-Dagan, V. Frydman, D. Zbaida, M. Morpurgo, R. Bar-Ziv, A single-step photolithographic interface for cell-free gene expression and active biochips Small 2007, 3, 500-510
9. J. D. Hoff, L. J. Cheng, E. Meyhofer, L. J. Guo, A. J. Hunt, Nanoscale protein patterning by imprint lithography Nano Lett. 2004, 4, 853-857
10. Hoeppener, S., Maoz, R. & Sagiv, J. Constructive microlithography: Electrochemical printing of monolayer template patterns extends constructive nanolithography to the micrometer-millimeter dimension range. Nano Lett. 3, 761-767 (2003).
11. Urbach, A. R. J., Love, C., Prentiss, M. G. & Whitesides, G. M. Sub-100 nm confinement of magnetic nanoparticles using localized, magnetic field gradients. JACS, 2003, 125, 12704-12705.
12. Bandic, Z. Z., Xu, H., Hsu, Y. & Albrecht, T. R. Magnetic lithography using flexible magnetic masks: applications to servowriting. IEEE Transactions on Magnetics, 39, 2231-2233 (2003).
13. McClelland, G. M., Hart, M. W., Renner, C. T., Best, M. E., Carter, K. R. & Terris, B. D. Nanoscale patterning of magnetic islands by imprint lithography using a flexible mold. Appl. Phys. Lett. 81, 1483-1485 (2002).

BACKGROUND OF THE INVENTION

The production of nano devices via common photolithography requires the application of short wavelength radiation and the use of special polymers that can be used as a photoresist. This approach presents significant engineering and material science challenges. The development of optical lithography in terms of resolution is indeed the limiting step in increasing the resolution and hence the density of features on semiconductor wafers [4]. However, photolithography faces serious challenges in further lowering of the minimum feature size. Shrinking critical dimensions in photolithography involves developing sophisticated and expensive systems and requires even more expensive tools in the future [5].

Chemical patterning of surfaces has become the focus of many studies [1, 6] and is widely used in bio-technological applications [7]. Chemical patterning of surfaces is performed by various methods varying from high-resolution, low-throughput techniques based on STM and/or AFM, to various printing-based methods [2,4-7,10], and to patterning methods based on photolithography [1]. Devices produced by combining both microelectronic processes and chemical patterning have also been developed. For bio-technological applications, various soft-lithography methods have been developed [8, 9]. The common feature in all these methods is that they use elastomer as the stamp, mold, or mask (rather than a rigid photomask) to generate micro patterns and microstructures. However, most of these techniques are limited to one stage, and sequential patterning on the same surfaces is very complex due to alignment problems. In addition, the methods commonly used for chemical patterning are not complementary for metal deposition, etching, and in general, for producing semiconductor-based devices.

In parallel, several different techniques have driven the advances in photolithography for microelectronic applications. Among those techniques are off-axis illumination (OAI), optical proximity correction (OPC), immersion lithography, and phase shifting mask technologies. Photomasks that use OPC or phase shifting are complex and extremely expensive to manufacture.

Most micron and sub-micron production processes are based on a top-down approach, with photolithography being an essential tool for patterning surfaces with high throughput [1]. When one attempts to pattern surfaces chemically, for molecular-based devices or for hybrid organic-semiconductor devices, photolithography is problematic, since it requires covering surfaces with photoresist that may contaminate or interfere with further chemical processes. Moreover, combining photolithography with chemical patterning requires removing the substrate from the adsorption solution, thereby exposing it to air and contamination. In addition, it is impossible with the current lithography techniques to pattern the inside of a tube or to induce a concentration gradient of adsorbed chemicals as a function of position on the substrate.

The ability to manipulate chemical species (e.g., chemical reagents) or biological species (e.g., cellular material, polymers, proteins, DNA, and the like) on a microscale is important in many applications. Such applications are in the fields of tissue engineering, biotechnology, microanalysis, and microsynthesis, amongst others. Depending on the application, the manipulations may involve positioning (e.g., patterning), separating, and/or transporting the species.

One approach to manipulating species involves the use of magnetic-based systems. Often, the targeted species contains or is embedded in a magnetic material (e.g., by tagging the species with magnetic beads) and the species can be attracted or separated using magnetic fields. In many cases, the species are attracted towards magnetic regions patterned on a substrate. Subsequently, the species may form patterns on the substrate defined by these magnetic regions.

An important difference between the common chemical processes occurring in solutions and chemistry in vivo lies in the sequential processes typical of biological systems. Namely, in vivo, space and time are separated in reactions occurring in a sequence, whereas in vitro, one has to separate the reactants and products physically in order to conduct sequential processes. This difference was bridged, however, when the concept of Lab-on-a-chip (LOC) was introduced. The microfluidic technology associated with micro-total analysis systems in LOC [11] has been developing rapidly and will undoubtedly revolutionize the chemical, pharmaceutical, healthcare, and food industries [12]. In a typical LOC system, the micro-channel is one of the most common and indispensable components, through which the sample's pre-concentration and separation or mixing can be realized. Consequently, the results of these processes can be delivered to the desired area to execute corresponding reaction and detection tasks [13]. Hence, a typical LOC element has two types of components: the micro-channels and the reaction/detection compartments.

GENERAL DESCRIPTION

The invention provides a novel patterning technique utilizing magnetic particles based on a "bottom-up" approach. It should be understood that while some known approaches enable positioning of chemical and/or biological species through the use of magnetic fields, these known techniques typically require magnetic components that are fabricated in, or on, a substrate and/or require the targeted species to contain or to be embedded in a magnetic material.

It should be noted that the generally known "bottom-up" chemical lithography approach has a relatively low throughput that can be overcome by very high parallelism that may be expensive and may introduce defects reducing the yield. Various "printing" schemes of such micro contact nanolithography have been developed [2] that can indeed be scaled to high throughput but are usually limited to a single stage of production and involve contact with the surface, which may affect other chemical processes. In contrast to other parallel lithography techniques such as nanocontact printing and nano-imprinting lithography [9], the Magneto Lithography (ML) method of the present invention is a backside lithography technique, which has the advantage of ease in producing multilayers with high accuracy of alignment and with the same efficiency for all layers.

Therefore, the current invention provides a method for patterning a substrate. The method comprises providing at least one magnetic pattern generator configured and operable to modulate a magnetic field (i.e. induce varying magnetic properties to a magnetic field) according to a desired pattern; applying the modulated magnetic field in the vicinity of the substrate (e.g. applying the magnetic field through the magnetic pattern generator) thus creating the magnetic field having the desired pattern of magnetic properties corresponding to a certain pattern of regions of interaction to be obtained on top of the substrate; and; interacting the substrate with magnetic particles, while under the application of the magnetic field, the magnetic particles being attracted to selected regions of interaction defined by the certain pattern while being substantially not attracted to regions outside the regions of interaction, thus creating on top of the substrate the certain pattern of regions interacted with the magnetic particles. The desired pattern corresponds to a certain pattern for a predetermined magnetic field profile and at a predetermined distance from the magnetic pattern generator, where the sample is to be located.

According to the teachings of the present invention, a magnetic field is applied to a substrate, where the magnetic field profile (intensity) varies in a predetermined manner within the substrate's plane. This can be achieved by using at least one magnetic pattern generator providing magnetic varying properties of a magnetic field applied thereon according to a desired pattern.

The magnetic pattern generator may include a physical element or elements accommodated between a magnetic field source and a substrate to be patterned; or may be constituted by operation of a magnetic field source to electronically affect the magnetic field properties (profile). Thus, in some embodiments, the magnetic pattern generator is a mask placed between a magnet (magnetic field source) producing the magnetic field, and the substrate, the mask being located either a topside or backside of the substrate or is spaced-apart from the backside of the substrate.

In some other embodiments, the magnetic pattern generator is based on the principles of hard disk devices used in computers, and enables to obtain electronically a magnetic field spatial pattern by changing the magnetic direction using a magnetic head. In this case, a magnetic head, similar to that existing in hard disks devices, is used to pattern the magnetic field onto a magnetic medium, in particular onto a hard disk medium. This is can be done by using a software translating a pattern (e.g. drawing patterned on the computer's screen) to magnetic shapes onto the magnetic medium e.g. the hard disk medium. The hard disk medium is then taken out from the hard-disk drive and used as a magnetic pattern generator. A thin metal or polymer film may be then deposited on top of the patterned hard-disk medium. Magnetic nanoparticles may then be used to cover the thin film applying either the negative or positive Magneto Lithography approach according to the teachings of the present invention, when the hard-disk medium is used as a magnetic pattern generator. After the patterning of the thin film, the film is taken off, and the hard disk can be reused.

Therefore, in some embodiments, the application of the magnetic field is carried out through a magnetic medium. The method comprises controllably changing a magnetic direction of the magnetic field to thereby electronically obtain a magnetic field spatial pattern on the magnetic medium; depositing a film on top of the patterned medium; interacting the magnetic medium covered by the film with magnetic particles, thus creating on top of the magnetic medium a patterned film. The electronic obtaining of the magnetic field spatial pattern comprises applying a computer algorithm for translating a predetermined data pattern into magnetic shapes on the magnetic medium.

The apparatus may comprise a control unit configured and operable to control the operation of a magnetic pattern generator to create a magnetic field spatial pattern corresponding to the certain pattern to be obtained on the substrate. The control unit may comprise a processor preprogrammed to translate a predetermined data pattern into a magnetic profile on the magnetic medium.

The mask may comprise a magnetic medium being patterned by the magnetic source operable by the control unit to change the magnetic direction of a magnetic field onto the magnetic medium enabling to electronically obtain the magnetic field spatial pattern. The magnetic medium may comprise a hard disk medium.

A magnetic field profile is thus patterned on a substrate, by using for example a permanent magnetic field applied perpendicular to the substrate. The magnetic particles are removed by removing the effect of the magnetic field.

For example, the magnetic pattern generator is a magnetic mask (e.g. paramagnetic metal mask or diamagnetic mask) defining the spatial distribution and shape of the applied field. This results in creation of a pattern of spaced-apart regions of the substrate capable of interacting with magnetic particles. The magnetic particles may be ferromagnetic nanoparticles.

Then, magnetic (nano) particles (NPs) interact with the substrate according to the field induced by the mask(s) (e.g. reside on the substrate according to the field induced by the mask), thus creating a pattern on the top surface of the substrate of spaced-apart regions of interaction between the substrate material and the particles. It should be noted that a magnetic field has the ability to control and direct magnetic NPs perpendicular to the surface. In this embodiment, the NPs do not bind chemically to the substrate, but held in position by the magnetic field. They serve the same role that the photoresist does in the conventional photolithography, while in contrast to photolithography process, in the ML technique of the present invention, the coating, exposure to energy, and the development of the resist, occur in a single-operation. After processing, namely, either deposition or etching, the NPs are washed away.

In some embodiments, the features (i.e. resolution) of the patterned surface exceed the features (i.e. resolution) of the mask. The method of the present invention also provides patterns whose width is narrower than the width of the lines in the mask when the method is applied in a non-equilibrium state, with short times and low concentrations of magnetic NPs. This is due to the gradient of the magnetic field within the line-width defined by the mask. Since the force applied on the NPs depends on the gradient of the magnetic field and the magnetic dipole moment of the NPs, it is possible to obtain patterned lines on the substrates that are thinner than the lines on the mask. Therefore, the pattern of regions interacted with the concentration-gradient of the magnetic particles has a characteristic dimension narrower than the corresponding characteristic dimension of the gradient of the magnetic field, such that features of the patterned substrate are smaller than features of the pattern of the magnetic field properties created by the magnetic pattern generator. The features of the patterned substrate may be of a sub-micron scale. In some embodiments, the size of the magnetic particles and the corresponding magnetic field are selected to obtain a uniform pattern. The features and the uniformity of the pattern are controlled by appropriately selecting duration of the application of the magnetic field and the concentration of the magnetic particles.

Therefore, the invention also provides for creating a gradient of adsorbate density so that the property of the surface is changing gradually as a function of position. For example, the surface is made hydrophobic gradually so that the gradient of hydrophobic interaction changes from scale of 10 nm up to mm. This can be achieved by applying a gradient of magnetic field on the surface. As a result, if the time of the process is controlled, a gradient of density of nanoparticles is obtained. Then, for example, molecules of type A are adsorbed between the nanoparticles, and after removal of the nanoparticles, molecules of type B are adsorbed on the area now free from particles. As a result, variation in the density of molecules A and B is obtained according to the gradient of the magnetic field. Therefore, in some embodiments, the method of the present invention comprises applying a gradient of the magnetic field to the vicinity of the substrate, interacting the substrate with the magnetic particles, creating the pattern of regions interacted with a concentration-gradient of the magnetic particles corresponding to a strength of the gradient of the magnetic field.

Similarly to photolithography, the method can be used for applying either a positive or a negative approach/mode. The pattern of regions interacted with the magnetic particles may thus be formed on the substrate using a positive and/or negative lithography.

In some embodiments (i.e. the positive mode), the magnetic particles react chemically or interact with the substrate via chemical recognition and/or biological recognition with the substrate. Hence, the magnetic particles are immobilized at selected locations, where the mask induces a magnetic field, resulting in a patterned substrate. In other embodiments (i.e. the negative mode), the magnetic particles are inert to the substrate, blocking the selected regions of interaction on the substrate from reacting with a reacting agent. Thus, a certain reacting agent can be further applied to the substrate within spaces between the regions of interaction. In this case, the magnetic particles do not interact chemically with the substrate and once they pattern the substrate, they block their site on the substrate. The exposed areas, not covered by the particles, can be covered by molecules that chemically bind to the substrate.

In some embodiments, the substrate is functionalized with a self-assembled monolayer.

In some embodiments, the method comprises interacting a reacting agent with the substrate; the magnetic particles blocking the binding of the reacting agent to the substrate, and removing the magnetic particles by removing the effect of the magnetic field, creating a negative patterned substrate.

The magnetic particles may be removed by physically displacing away the magnetic pattern generator. This can be applied in combination with other removing methods like sonication and washing.

In some embodiments, the method comprises interacting a first reacting agent with the substrate via chemical recognition and/or biological recognition; interacting the substrate covered by the first reacting agent with magnetic particles being attracted at the selected regions of interaction; interacting a second reacting agent with the substrate; the magnetic particles blocking the recognition between the first agent and the second reacting agent, and removing the magnetic particles creating a negative patterned substrate.

In other embodiments, the method comprises providing a second magnetic pattern generator being configured and operable to provide a magnetic varying properties of a magnetic field applied thereon according to a second desired pattern; applying a magnetic field to the vicinity of the substrate with the certain pattern through the second magnetic pattern generator thus creating a second pattern of magnetic field on top of the substrate; and interacting magnetic particles with the substrate, while under the application of the magnetic field, the particles being attracted at second selected regions of interaction defined by the second desired magnetic pattern, creating a second pattern of spaced-apart regions interacted with the particles on top of the substrate with the certain pattern.

It should be understood that according to the invention the creation of such pattern of spaced-apart regions of interaction does not require any physical contact between the mask and the substrate, and does not create any surface relief on the substrate. The mask may have a non-planar surface. The magnetic field pattern creating the interaction pattern is applied in the vicinity of the substrate. The interaction pattern may be applied to the substrate within a medium which may be gas (air) or a solution. The substrate may be immersed in a solution containing magnetic particles and/or one or more a reacting agents.

The present invention enables to chemically pattern surfaces with sub-micron resolution. The Magneto-Lithography (ML) method of the present invention simplifies chemical surface patterning, since it does not require resist, which may contaminate the substrate, and therefore allows fast patterning of large surfaces without having to face contamination problems or the need to remove the substrate from the solution. In addition, the ML method of the present invention does not depend on the surface topography and planarity (i.e. is not affected by the topography or planarity of the surfaces) and can be therefore performed on rough surfaces and allows the chemical patterning of the inside of tubes as will be detailed further below According to the technique of the present invention, neither magnetic particles nor magnetic mask is a part of material to be adsorbed onto a substrate and a part of the substrate. Also, the present invention provides for patterning surfaces which are not (easily) accessible by material deposition/removal processes of the chemical lithography and also photolithography, such as patterning of the inner surface of a tube. The substrate may be a non-planar surface and in particular, a tube, the particles being attracted at selected regions of interaction on an inner surface of the tube defined by the desired pattern thus creating in the inner surface of the substrate a pattern of regions interacted with the particles. Since a magnetic mask is applied, it is possible to have high production throughput. Unlike other lithography methods, the method can be applied also as a backside lithography, which has the advantage of ease in producing multilayers with high accuracy of alignment and with the same efficiency for all layers, regardless to the number of layers. Moreover, the method allows the formation of a multi-step process without removing the substrate from a solution. This feature is advantageous for bio-related applications when reactants have to be kept at controlled conditions. The reacting agent may thus comprise bio-molecules. Therefore, the positive and negative ML can be applied on a wide range of surfaces for patterning with either small or large molecules or with bio-molecules sensitive to the chemical environment.

In some embodiments, the mask can be patterned with diamagnetic lines, which create a magnetic field in opposition of the externally applied magnetic field. The mask may include both diamagnetic and paramagnetic lines to form any required magnetic field on the substrate.

As indicated above, the invention advantageously provides for chemically patterning the inside of a tube. This allows the tube to operate as a sequential reactor in which molecules of a certain reacting agent that flows through can react sequentially with the inner surface within the regions thereof that were covered by magnetic particles. To this end, the magnetic field keeping the magnetic particles attracted to the surface region is sequentially applied to successive regions of the tube.

There is also provided a method for producing microelectronic devices comprising the method as described above; placing the substrate in an etcher for a certain time, the pattern of regions interacted with the particles being used as an etching mask and removing the magnetic particles by removing the effect of the magnetic field thereby creating a pattern of etched regions. The pattern of etched regions has a characteristic dimension narrower than the corresponding characteristic dimension of the gradient of the magnetic field, such that the feature size of the pattern on the substrate is smaller than that of the pattern created by the magnetic pattern generator.

Moreover, the invention enables the unification of two elements a micro-channel and reaction compartments, into a third type of element, a tube reactor, which combines the properties of both. This is achieved by utilizing the Magneto-Lithography (ML) method, which allows the chemical patterning of the inside of the micro-channel tube. Therefore, the invention enables chemical and biochemical patterning of the inner tube surfaces, especially when using tubes with a small diameter as efficient reactors for LOC. LOC functions can be performed within the micro-channel, thereby reducing production time and reducing the amount of material that has to be processed. The new element (i.e. tube reactor) allows to perform sequential processes by applying a very simple and inexpensive technique. By patterning the inside of the tube with enzymes or reactants, the tube may be used both as a transport element and as a reactor in which the substrate in the solution reacts with the molecules that were adsorbed earlier on the tube's internal surface.

In some embodiments, the method comprises applying a magnetic field sequentially to successive regions of the substrate.

In other embodiments, an array of electrically conductive wires can be used as a mask. When current flows through the wires, a magnetic field is created in the vicinity thereof. By switching the current flow sequentially it is possible to adsorb particles step-after-step to different regions of the mask. This is a so-called "dynamic mask" that either does not require the application of magnetic field, since the magnetic field induced by the current flowing through the wires is sufficient, or can be used in combination with permanent magnetic field to alternate the magnetic field by applying additional field through the current flowing through the wires. The method of the present invention may comprise switching sequentially the current flow on the wires, to switch the magnetic field inducing a sequential patterning.

Moreover, as explained above, there is a need in the art to provide a single patterning method to be applied for high-resolution (i.e. on a scale of tens of nanometers), high-throughput production of microelectronic devices as well as chemical patterning applications as separate processes or as combined processes. The ability to use the same method for all types of surface patterning simplifies production processes related to the applications combining electronics with chemical/bio-recognition processes.

The ML method of the present invention may be applied to common microelectronic processes such as etching and deposition and/or ion implantation processes.

By applying three-dimensional masks, it is possible to obtain high-density patterned surfaces and to correct adjustment of various parameters and to use sub-10 nm diameter magnetic particles with a strong magnetic field enables to provide critical dimension comparable or even smaller than those available with conventional photolithography methods. The method thus enables creation of microelectronic devices of size smaller than current critical sizes (not limited by the parameters of the optical-lithography) and chemical and/or biomaterial patterning of surfaces with sub-100 nm resolution. Sequential processes can be used and it can be applied to non-planar surfaces It should be noted that the ML technique of the present invention is not limited to the production of magnetic devices, as reported previously for magnetic-based lithography methods [10].

The invention also provides, as one of its broad aspects, a patterned structure manufactured by the method as described above. According to another broad aspect of the invention, there is provided an apparatus for patterning a substrate. The apparatus comprises a magnetic field source for generating a magnetic field, and at least one magnetic pattern generator configured to modulate the magnetic field to provide magnetic varying properties of the magnetic field according to a desired pattern corresponding to a certain pattern to be obtained on the substrate.

In some embodiments, the magnetic source is a multi-peg magnet or a magnet surrounding the substrate being tube. The tube is configured and operable as a tube reactor enabling to perform sequential reactions within the tube reactor.

In some embodiments, the present invention provides the ability to use the patterned substrate for catalyzing a reaction in a solution reaction in spatially localized regions. The first reacting agent may comprise a catalyst, creating patterned regions of the catalyst to thereby use the patterned substrate for catalyzing at least one chemical reaction in spatially localized regions. The catalyst may include enzymes such that the chemical reaction is an enzymatic reaction. The first reacting agent may include a first enzyme and the second reacting agent may include a second enzyme to thereby induce sequential enzymatic reactions. In particular, by using the ML method of the present invention, it is possible to localize protein at a predefined spot on a surface with a resolution of sub-100 nm. The patterned regions of the catalyst may thus include at a predefined spot. This is can be performed by using negative ML for self-assembly of a line of hydrophobic monolayers onto a flat gold surface covered with a hydrophilic monolayer.

BRIEF DESCRIPTION OF THE DRAWINGS

The patent or application file contains at least one drawing executed in color. Copies of this patent or patent application publication with color drawings will be provided by the Office upon request and payment of the necessary fee.

In order to understand the invention and to see how it may be carried out in practice, embodiments will now be described, by way of non-limiting example only, with reference to the accompanying drawings, in which:

FIG. 2a represents a line-patterned mask with a 20-μm space between the lines used in the Magneto-Lithography (ML) method of the present invention;

FIGS. 2b-2e represent SEM images of a positive ML pattern onto gold-coated glass substrates functionalized with a self-assembled monolayer of 1-4 Benzendimethanethiol, using the line-patterned mask of FIG. 2a;

FIG. 4a illustrates the fluorescence of Av-FITC molecules adsorbed on a glass substrate, the co-centered dark ring patterns are the regions in which the magnetic NPs were blocked using the negative ML approach of FIG. 3;

FIG. 4b illustrates the fluorescence following the disappearance of the outer ring pattern, after the substrate was exposed to Av-FITC with no magnetic field using the negative ML approach of FIG. 3;

FIG. 4c represents the fluorescence intensity profile along the dashed lines shown in FIG. 4a and FIG. 4b;

FIG. 7a is obtained after adsorbing 50 μg ml$^{-1}$ magnetic NPs and exposing the substrate for 2 minutes to a magnetic field; FIG. 7b is obtained after adsorbing 5 μg ml-1 magnetic NPs and exposing the substrate for 2 minutes to a magnetic field; FIG. 7c is a SEM image of a uniform 30-nm line-width pattern of GFP and FIG. 7d is a three-dimensional image of the line shown in FIG. 7c;

FIGS. 12a-12d are SEM images of the patterns obtained by the etching process obtained after exposing the substrate for 5 minutes to solutions of nanoparticles in the different concentrations FIGS. 13a-13e are SEM images obtained after deposition of 50 nm Cr, using the method of the present invention; in particular FIG. 13a is a SEM image of a mask used for patterning the substrate with magnetic nanoparticles; FIG. 13b is a SEM image of the magnetic nanoparticles after they were assembled onto the substrate according to the field induced by the mask; FIG. 13c is a SEM image of nanoparticles assembled on one site as marked in FIG. 13b by a dashed circle; FIGS. 13d-13e are SEM images of the resulting structure following a lift-off process in which the nanoparticles were removed;

FIG. 14a is a light microscope image of a pattern onto a gold substrate; FIG. 14b is a SEM image of pattern onto a gold substrate; FIGS. 14c-14d are SEM images of the same with high resolution patterning.

FIG. 15b is an image showing the fluorescence of both fluorescein and sulforhodamine observed from two bands of the nanoparticles adsorbed within a tube patterned by the positive ML process of FIG. 15a;

FIG. 16b is an image the fluorescence observed from a tube patterned by the negative ML process of FIG. 16a;

DETAILED DESCRIPTION OF EMBODIMENTS

Figure 1A:
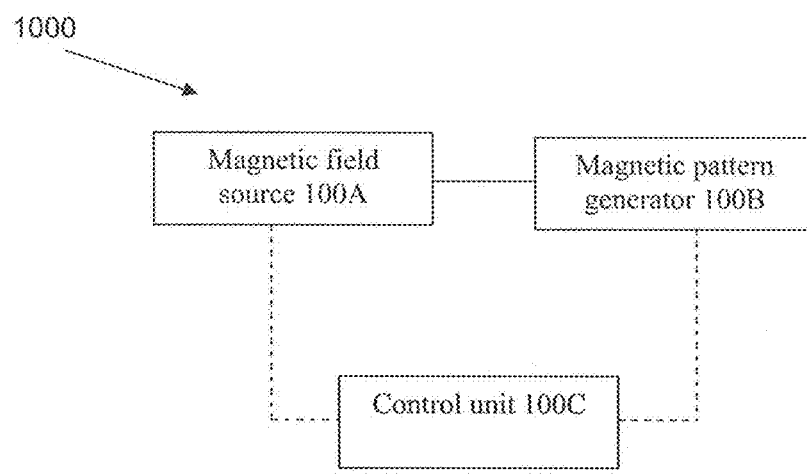
FIG. 1a is a general schematic representation of the magnetic patterning method of the present invention.

Reference is made to FIG. 1a exemplifying an apparatus of the invention for patterning a substrate. The apparatus 1000 includes a magnetic field source 100A for producing a magnetic field, and one or more magnetic pattern generators, single such generator 100B being shown in the figure. The magnetic pattern generator 100B is configured to appropriately modulate the magnetic field to provide magnetic varying properties of a magnetic field according to a desired pattern. The magnetic pattern generator 100B may include or be constituted by a physical element, i.e. static mask (e.g. magnetic mask, or previously patterned hard disk medium); or an electronic modulator inducing variation of a magnetic field profile, i.e. the so-called "dynamic" or virtual" mask. Thus, magnetic field source 100A and magnetic pattern generator 100B operate together to produce a magnetic field modulated in accordance with the desired pattern corresponding to a certain pattern to be obtained on the substrate.

Also preferably provided in the apparatus 1000 is a control unit 100C. The latter is typically a computer system including inter alia data input/output utilities, data processing and analyzing utility, and a memory utility. For example, in the case of dynamic or virtual mask, the control unit (i.e. its processor) operates to translate a predetermined data pattern (stored in the memory utility) into a magnetic field profile creating a certain pattern (shape) on a substrate, e.g. a film deposited onto an intermediate pattern on a magnetic medium (e.g. previously patterned hard disk medium).

Figure 1B:
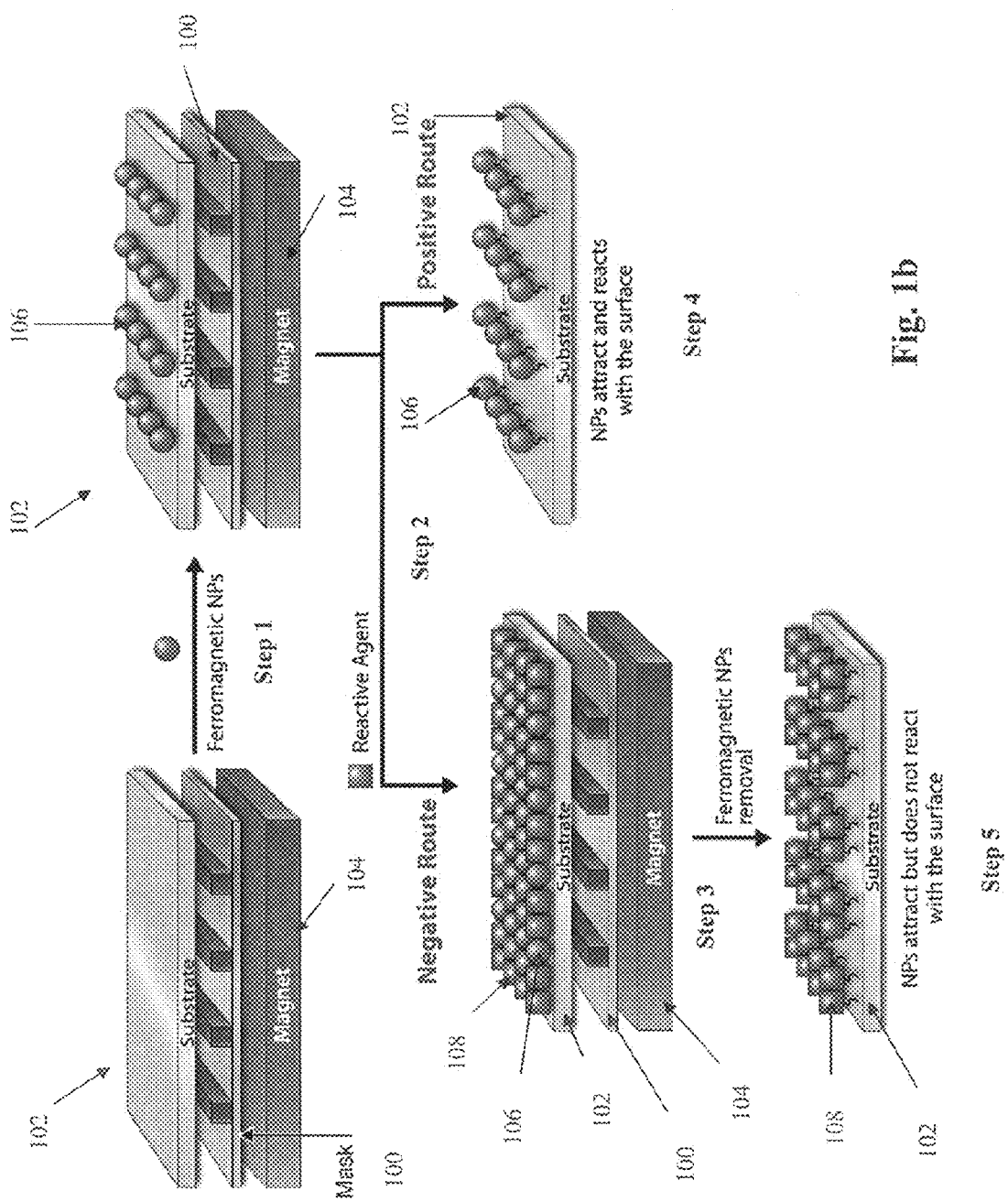
FIG. 1b is a schematic representation of the Magneto-Lithography (ML) method of the present invention for the positive and negative approaches.
Figure 2F:
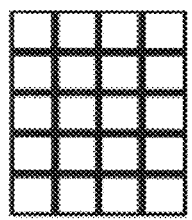
FIG. 2f represents a grid-patterned mask with a 20-μm space between the lines used in the Magneto-Lithography (ML) method of the present invention.
Figure 2H:
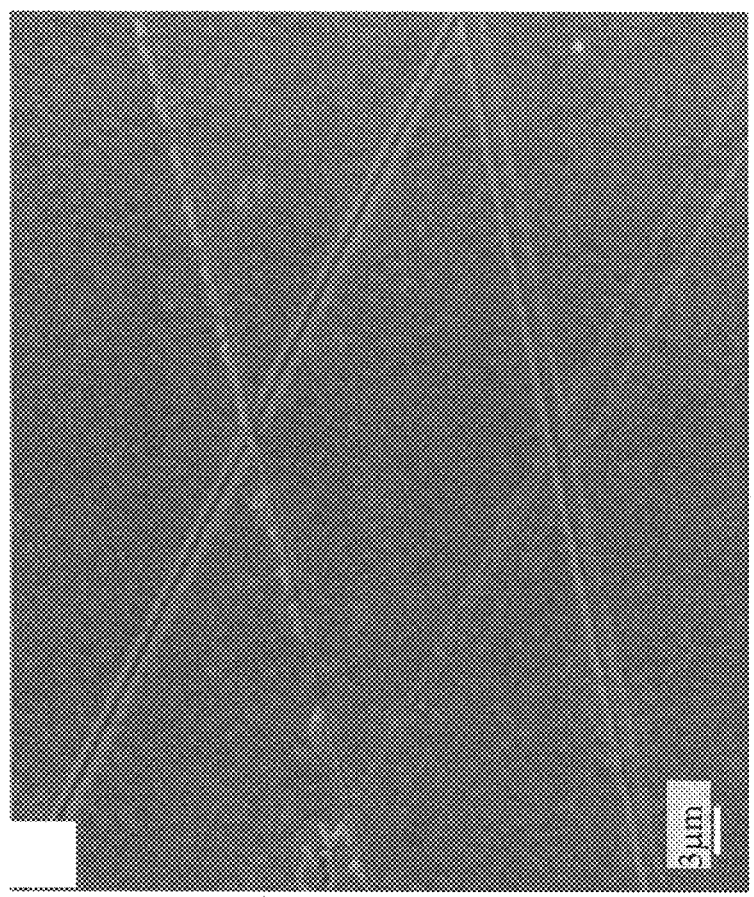
FIGS. 2g-2h represent SEM images of a positive ML pattern onto gold-coated glass substrates functionalized with a self-assembled monolayer of 1-4 Benzendimethanethiol, using the grid-patterned mask of FIG. 2f.
Figure 2G:
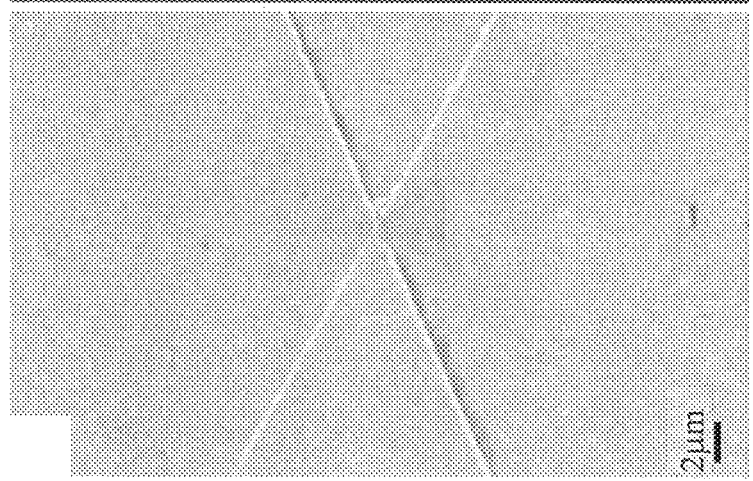

Reference is made to FIG. 1b showing a specific but limiting example for both the positive and negative ML processes of the present invention. The technique is performed as follows:

In step 1, a magnetic field pattern is created in the vicinity of a substrate 102 which is to be "chemically patterned". In the present example, this is implemented by using a magnetic mask 100 which is placed at the backside of substrate 102, i.e. at its surface opposite to that which is to be patterned. The mask is configured in accordance with a pattern of regions of interactions as described above. A magnetic field, generated by a magnet 104 (e.g. permanent) set under the mask 100, is then applied to the substrate 102 through the mask 100 which defines the spatial distribution and the shape of the applied field. Thus, the mask 100 induces a magnetic field toward the substrate 102 through the pattern of the mask. In step 2, ferromagnetic nanoparticles (NPs) 106 interact with the substrate 102 according to the field defined by the mask 100. In this example, such interaction is achieved via deposition of particles onto the substrate 102.

In the positive approach (step 4), the ferromagnetic NPs 106 react chemically or interact via chemical recognition with the substrate 102. Hence, the ferromagnetic NPs 106 are immobilized only at selected locations (regions of interaction) where the mask 100 induces a magnetic field, resulting in a patterned substrate.

In the negative approach (steps 3, 5), the ferromagnetic NPs 106 are inert to the substrate 102. Hence, once they are deposited onto the substrate 102, the NPs 106 block their binding site on the substrate 102 from reacting with another reacting agent 108, as illustrated in step 3. After the adsorption of the reacting agent 108, the NPs 106 are removed (step 5), resulting in a negatively patterned substrate 102.

It should be noted that interaction between the magnetic particles and the substrate is interrupted after removal of the effect of the magnetic field. This can be implemented by physically displacing the magnetic mask away from the substrate (e.g. in case the mask regions are ferromagnetic), or by switching off the magnetic field applied through a stationary mounted mask (e.g. in case the mask regions are paramagnetic).

Reference is made to FIGS. 2a-2h illustrating a specific but non-limiting example of a positive ML patterning using the teachings of the present invention, in which gold-coated glass substrates functionalized with a self-assembled monolayer of dithiols (1-4 Benzendimethanethiol) were used. Cobalt masks were produced for magnetic field patterning of the substrate. It should be noted that the assembly of cobalt nanoparticles (NPs) can be induced by a magnetic field, in order to generate cobalt supercrystals [3]. Two masks were used: one patterned with lines (FIG. 2a) and the other with a grid (FIG. 2f), both with a 20-µm space between the lines. A magnetic field of 100 G was induced through the cobalt mask by a permanent magnet, while the substrate was immersed into a solution of $FeO_4$ NPs (10-nm diameter) for 15 minutes. Then the mask was removed and the substrate was washed. Since the $FeO_4$ NPs react with the thiol group exposed on the surface, the result of the positive ML is a copy of the mask pattern on the substrate. Due to the interaction with the magnetic field, the NPs are selectively attracted to the surface sites where the field is the largest and react with thiol function groups of the monolayer at these locations. These images show 1-5-µm-wide lines with a 20-µm space between them. It should be understood that by carefully tuning the deposition time, the patterns having a width narrower than the width of the lines in the mask can be obtained. This is due to the gradient of the magnetic field within the line-width defined by the mask. The magnetic field is stronger in the center than at the edges. As a result, the NPs are first organized in the center of the line.

The negative ML approach of the present invention can be conducted by several methods. For example, magnetic NPs can be blocked by the binding of biotin molecules to a glass surface, or, alternatively, the adsorption of a biotin monolayer can be blocked onto a substrate by magnetic NPs and then the magnetic NPs can be used to block the biotin-avidin bio-recognition process.

Figure 3:
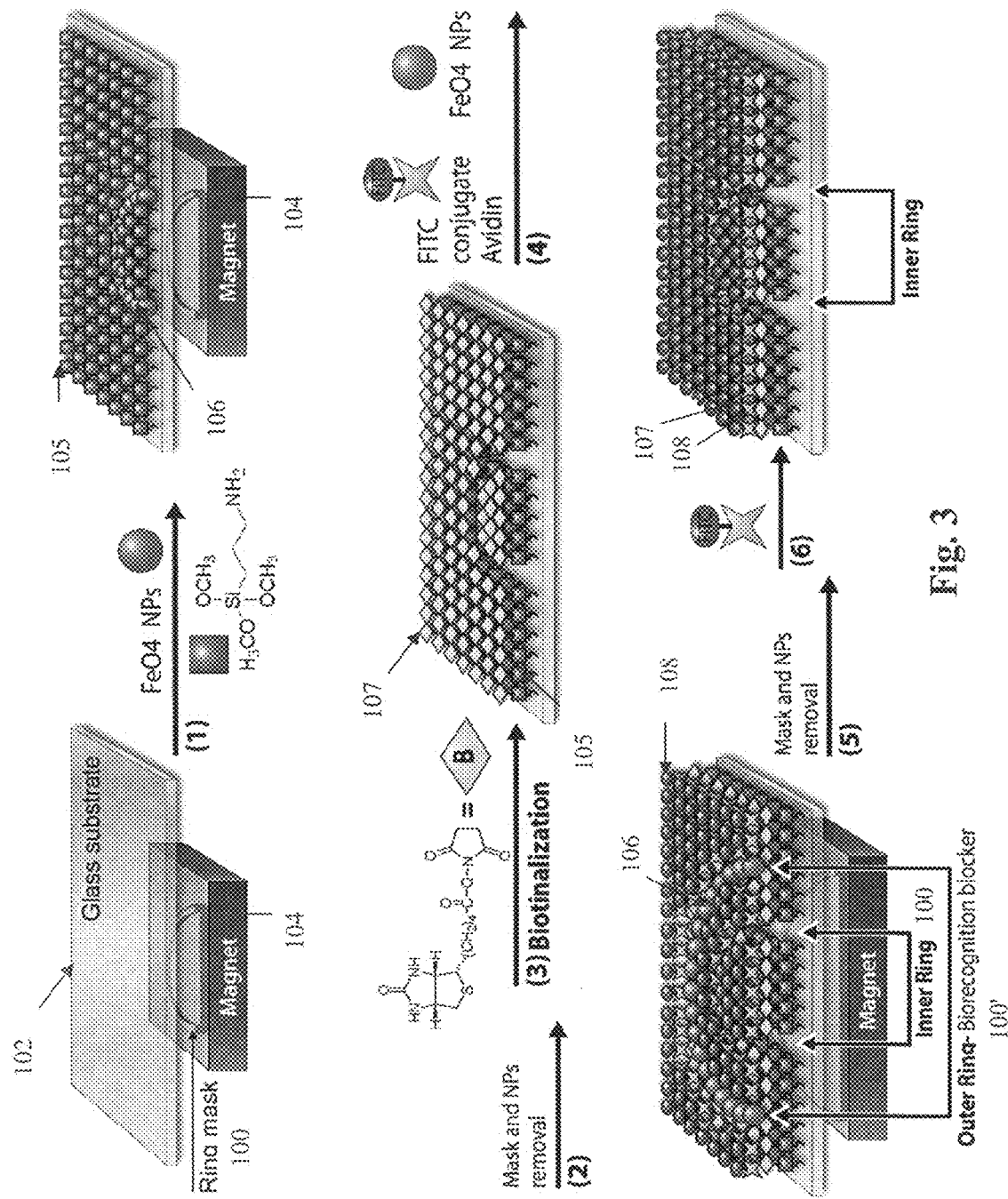
FIG. 3 is a schematic representation illustrating the negative ML approach according to the teachings of the present invention, for assembly of a Biotin-Avidin monolayer on a glass surface using an iron ring mask.

Reference is made to FIG. 3 exemplifying a negative ML approach in which a glass substrate 102 is exposed to a ring-shape patterned magnetic mask 100 in a solution containing trimethoxyaminosilane 105 and $FeO_4$ NPs 106. In step 1, the magnetic NPs 106 are attracted to sites at which the magnetic field is stronger and protect these locations (i.e. regions of interaction) from reacting with aminosilane 105 in the solution. FeO$_4$ NPs 106 are inert with respect to a glass substrate and therefore are attracted to the selected regions of the substrate by magnetic field much quicker than a chemical adsorption of trimethoxyaminosilane to the substrate. Hence, providing a mixture of trimethoxyaminosilane and FeO$_4$ NPs in the solution is possible in this example. Thus, the inert FeO$_4$ NPs 106 are organized onto the glass substrate 102 according to the magnetic field applied by the ring-patterned mask, This process results in selective silanization of locations of the surface that were not covered with the NPs 106. Since the magnetic NPs 106 are inert to the bare glass surface, they can be removed from the surface (e.g. by washing or air flow), after the magnetic mask/field (step 2) is removed. In the next step (step 3), the substrate was biotinylated with NHS-biotin 107 (N-hydroxy-succinimide-biotin) which reacts with the amino functional patterned surface.

In order to demonstrate the success of the method of the present invention in multiple stages of patterning, the prepared biotinylated glass surface was exposed to a second magnetic mask 100' with a ring pattern. The second ring-shaped patterned magnetic mask 100' is larger and is co-centered with the previous ring-shaped mask 100. The substrate 102 was then exposed to a solution of fluorophore-labeled avidin (Av-FITC) 110 and magnetic NPs 106 (step 4). Again, the magnetic NPs 106 were attracted by the magnetic field applied by the ring-patterned mask and therefore were assembled as a ring. Hence, the biotin groups 107 underneath the NPs 106 were protected and did not interact with the Av-FITC 110. The result of this negative ML process is a patterned surface with two co-centered rings. The inner ring represents the negative ML, where a reaction between molecules and the substrate is prevented, whereas the outer ring prevents the interaction between the already adsorbed molecules and molecules in the solution. The second negative ML process is reversible, since the removal of the magnetic mask 100' causes magnetic NPs to leave the ring sites (step 5). Hence, the biotin groups 107 at these sites are deprotected and the Av-FITC molecules 110 in the solution can interact with biotin groups 107 (step 6). However, this is not the case when a negative ML is performed during adsorption directly on the glass substrate.

Reference is made to FIG. 4a illustrating the fluorescence of Av-FITC molecules adsorbed on a glass substrate in the negative ML approach illustrated in FIG. 3, the co-centered dark ring patterns are the locations in which the magnetic NPs were blocked. The inner ring was formed by the magnetic NPs that blocked the binding of biotin molecules to the glass surface, whereas the outer ring was formed by the magnetic NPs that blocked the biotin-avidin bio-recognition process.

FIG. 4b illustrates the fluorescence following the disappearance of the outer ring pattern, after the exposition of the substrate to Av-FITC with no magnetic field.

FIG. 4c illustrates the fluorescence intensity profile along the dashed lines shown in FIGS. 4a and 4b. The intensity profile along the dashed line in (a) is denoted as a line 200. The area 202 represents the intensity profile along the dashed line in (b) after the outer ring disappeared as a result of exposing the substrate to Av-FITC with no magnetic field. The fluorescence intensity profile along the pattern (the dashed line) illustrates the irreversible nature of the negative ML process as seen in the inner ring pattern, which remains dark even after being treated with Av-FITC in the absence of a magnetic mask. The inner ring shows negligible nonspecific adsorption of Av-FITC, which proves the deficiency of biotin groups in this area caused by the negative ML. The outer ring pattern, on the other hand, disappears after the substrate is exposed to Av-FITC, with no magnetic field. This is because the pre-adsorbed biotin molecules were deprotected, by removing the NPs, after removing the magnetic field, and could bind the Av-FITC. Hence, this process is reversible.

Figure 5:
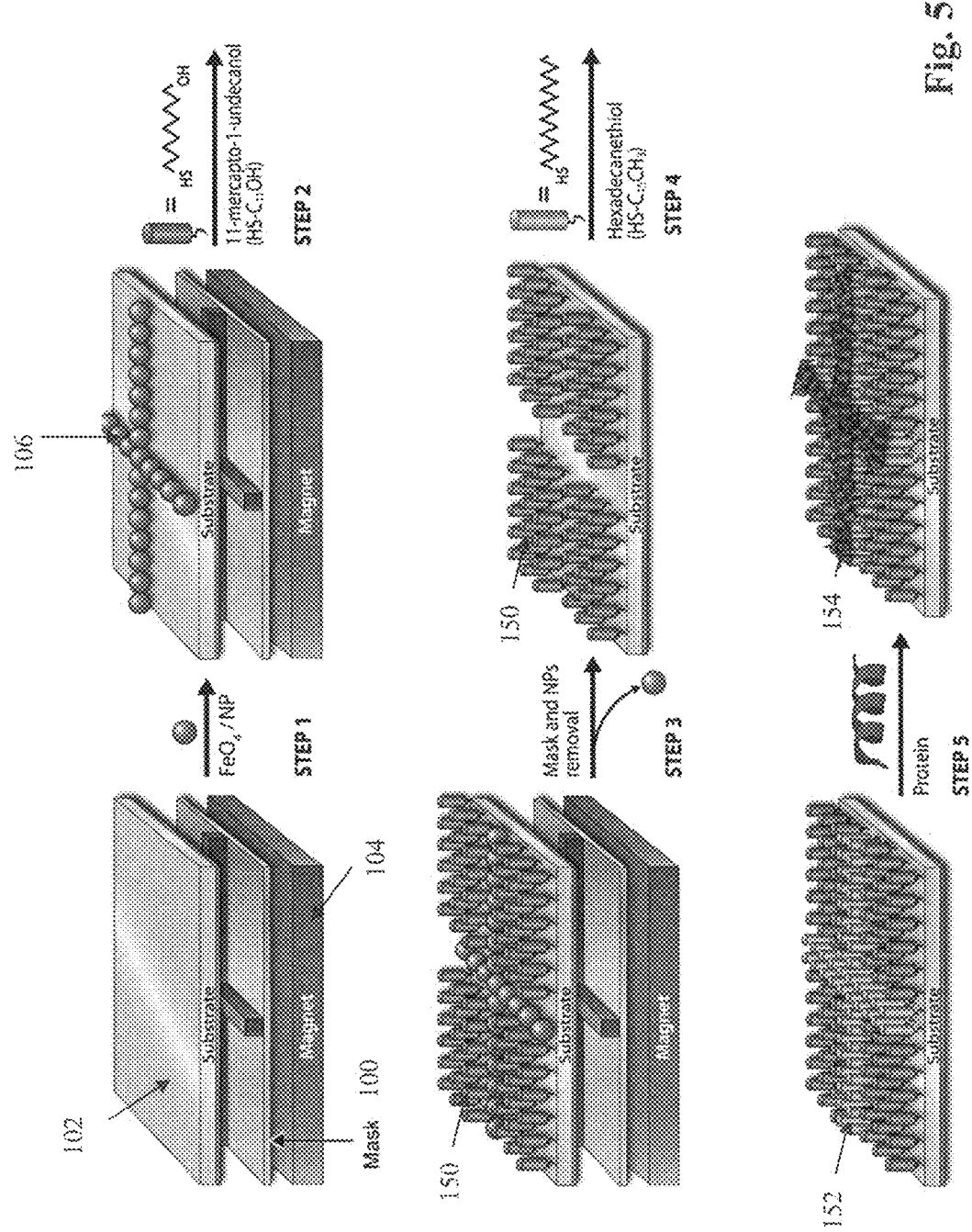
FIG. 5 is a schematic representation of the Magneto-Lithography (ML) method of the present invention for patterning gold-coated silicon by hydrophobic/hydrophilic monolayers.

Reference is made to FIG. 5 illustrating the patterning of gold-coated silicon substrates by hydrophobic/hydrophilic monolayers by using a negative mode of the ML method of the present invention. Lines of hydrophobic molecules were patterned on a surface covered with hydrophilic molecules. Then the surface was exposed to GFP and washed. A series of 200-nm thick gold substrates were coated with self-assembled monolayers composed from mixtures of hydrophobic/hydrophilic reagents. Different molar fractions of the hydrophobic/hydrophilic reagents were used to gradually change the hydrophobicity of the gold substrates.

A magnetic field pattern is created in the vicinity of a substrate 102 by using a magnetic mask 100 which is placed at the backside of substrate 102, i.e. at its surface opposite to that which is to be patterned. A magnetic field, generated by a permanent magnet 104 set under the mask 100, is then applied to the substrate 102 through the mask 100 which defines the spatial distribution and the shape of the applied field. Thus, the mask 100 induces a magnetic field toward the substrate 102 through the pattern of the mask. In step 1, inert ferromagnetic nanoparticles (NPs) 106 (e.g. Fe$_3$O$_4$ 10 nm diameter, dissolved in toluene) are attracted to a gold substrate 102 (e.g. a silicon substrate (300 μm thick) that was coated with a high-quality gold layer of 200 nm by an e-beam evaporator), according to the field profile defined by the mask 100. In this example, such interaction is achieved via deposition of particles onto the substrate 102. Next, hydrophilic reacting agent/reagent 150, with a hydroxyl head group, 11-mercapto-1-undecanol (11MUD=HS—C$_{11}$OH), is self-assembled onto the substrate at places not covered by the NPs (Step 2). The NPs 106 block their binding site on the substrate 102 from reacting with the hydrophilic reacting agent 150. After the adsorption of the hydrophilic reacting agent 150, in step 3, the magnetic mask 100 is removed and the substrate 102 is sonicated and washed in order to remove the magnetic NPs 106. Subsequently, in step 4, a hydrophobic reacting agent 152, hexadecanethiol (HDT=SH—C$_{15}$CH$_3$), is adsorbed on the substrate 102 in the areas previously covered by the NPs 106. In this specific and non-limiting example, both molecules, HDT and 11MUD, are dissolved (10 mM solution) in ethanol; the adsorption time is 3 hours at room temperature. For verifying the patterning of the hydrophobic reacting agent, a green fluorescent protein (GFP) was used to verify whether the GFP interacts stronger with hydrophobic surfaces than with hydrophilic surfaces. In the last stage (Step 5) the surface was exposed to GFP 154 that was adsorbed on the hydrophobic lines 152 and was repelled from the hydrophilic background 150.

Figure 6:
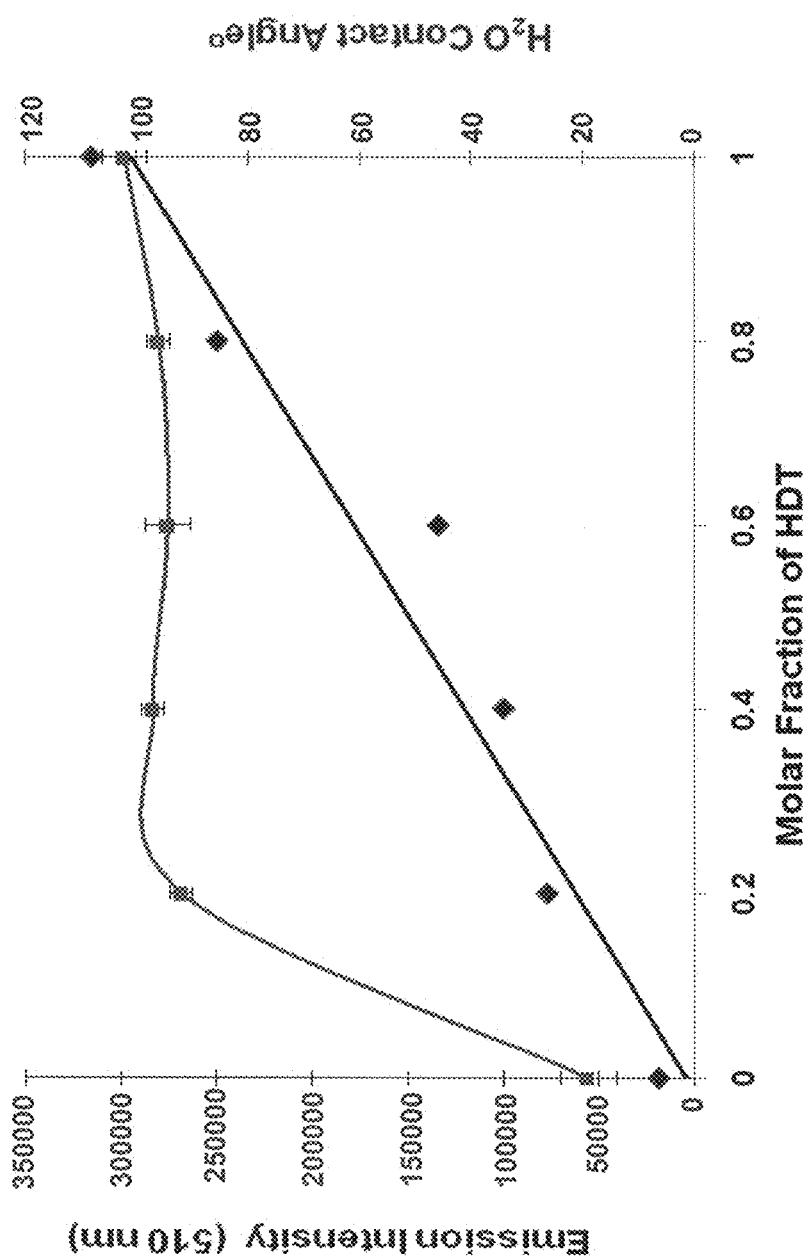
FIG. 6 is a graph illustrating the comparison between receding contact angles (CA) measured with water droplets and fluorescence intensity at 510 nm measured from a GFP, after monolayer-covered substrates were immersed in a GFP solution.

Reference is made to FIG. 6 comparing receding contact angles (CA) measured with water droplets and fluorescence intensity at 510 nm, measured from GFP after monolayer-covered substrates were immersed in a 10-nM GFP solution for 30 minutes. As seen in the figure, there is an abrupt jump in the contact angle at a molar fraction of 0.2 HDT. Following this change, the CA remains constant. This step-like change in the contact angle may indicate a phase separation in which each of the molecules forms a domain that includes only one type of molecules. The water droplets are averaged over a large area and therefore are affected by the hydrophobic domains; therefore, they have large contact angles in the case of monolayers made from the hydrophilic/hydrophobic mixtures. The monitoring of the fluorescence from the GFP shows that the amount of GFP on the surface is linearly correlated with the molar fraction of HDT. This finding is again consistent with the formation of separate domains for each molecule. The GFP is adsorbed better on the hydrophobic domains and therefore as their concentration increases, more GFP is adsorbed and more fluorescence is observed. Hence, GFP efficiently serve for the detection of hydrophobic patterns on a nanometer scale.

Figure 7A:
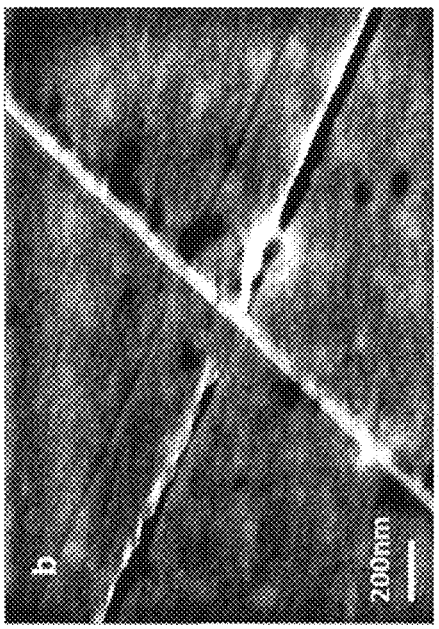
FIGS. 7a-7d are SEM images of a patterned surface, after exposition to GFP; in particular
Figure 7C:
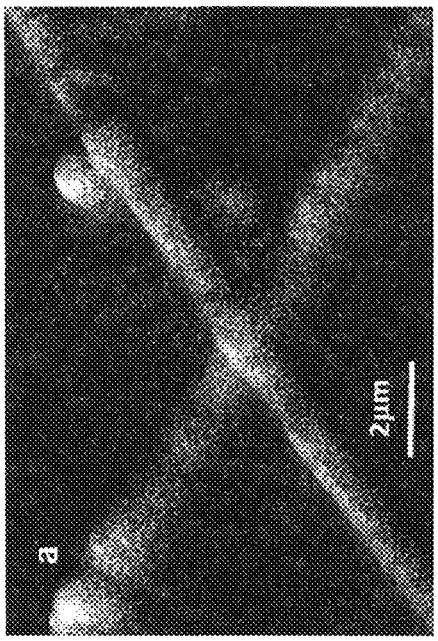
Figure 7B:
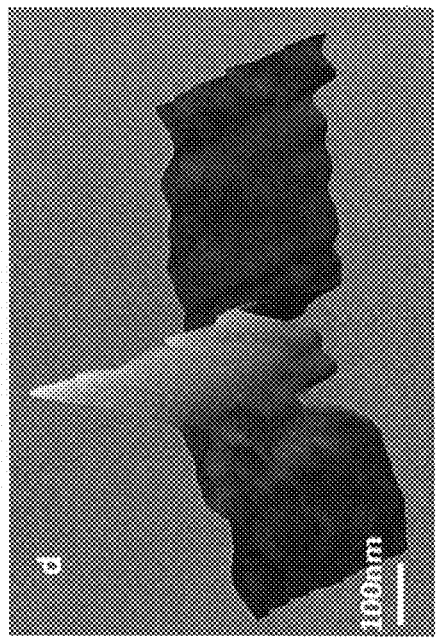

FIGS. 7a-7d are SEM images of the patterned surface made in the process described in connection with FIG. 5, after it was exposed to GFP, The GFP appears as a bright line, as already reported before, for SEM images of proteins. In FIG. 7a, a low-resolution (more than 1 μm wide) line was obtained after adsorbing a high concentration (50 μg ml$^{-1}$) of magnetic NPs that were exposed for 2 minutes to the magnetic field. As illustrated in FIG. 7b, a much narrower is line, with a width of about 30 nm, was obtained when a dilute (5 μg ml$^{-1}$) solution of magnetic NPs was used and exposed again to the magnetic field for 2 minutes. The protein is adsorbed on the hydrophobic lines and is repelled from the hydrophilic background.

Figure 7D:
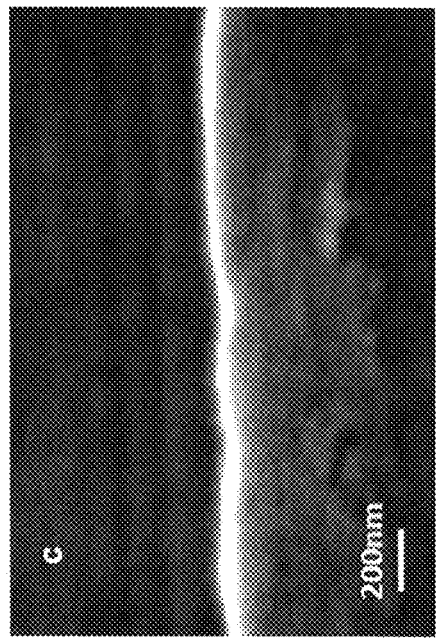

FIG. 7c is a SEM image of a uniform 30-nm line-width pattern of GFP and FIG. 7d is a three-dimensional image of the line shown in FIG. 7c.

It should be understood that the 30-nm molecular patterning was achieved despite the fact that the lines in the magnetic mask 100 that induced the magnetic field had a width of 50 μm. The higher resolution was obtained by either reducing the concentration of the NPs, as shown in FIGS. 7a-7b, or by shortening the adsorption time, so that the system does not reach equilibrium. Under these conditions, the NPs are first adsorbed in the high field part, namely, only at the center of the magnetic line. This is because the gradient of the magnetic field, within the line-width defined by the mask, is stronger in the center than at the edges of the mask lines as will be further detailed below in connection with FIGS. 8a-8b.

Figure 8A:
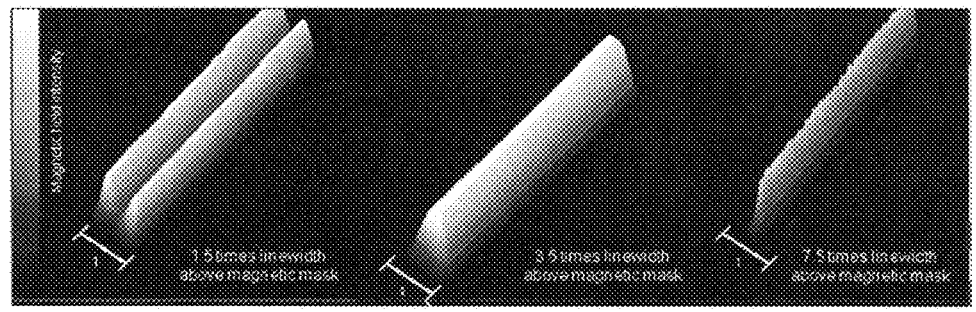
FIG. 8a illustrates a magnetic field distribution on top of a magnetic mask line width at distances corresponding to 1.5, 3.5 and 7.5 times the linewidth of the pattern on the mask.
Figure 8B:
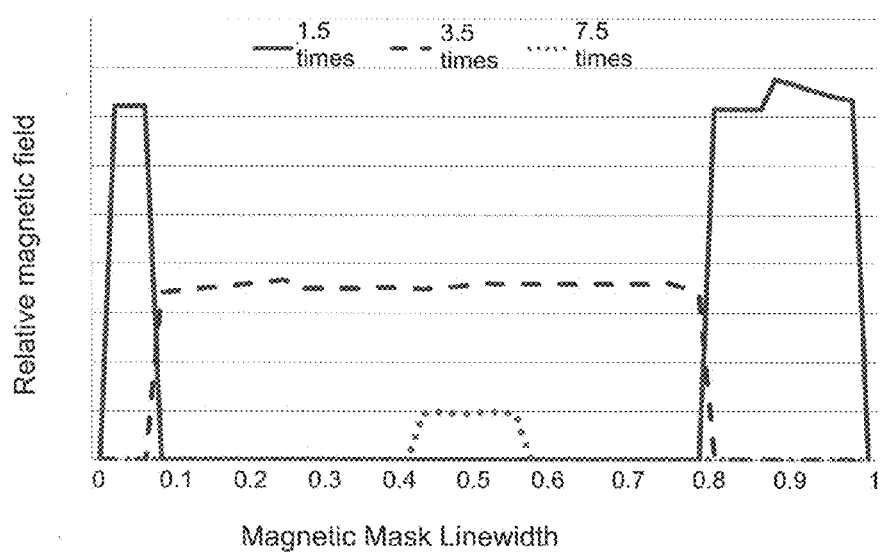
FIG. 8b is a graph showing the sites having a magnetic field with the strongest intensity at distances corresponding to 1.5, 3.5 and 7.5 times the linewidth of the pattern on the mask.

FIGS. 8a-8b shows the results of a simulation of a magnetic field on a mask as a function of the distance from the mask. The magnetic field distribution above the mask is calculated by using the COMSOL program. FIG. 8a illustrates a magnetic field distribution on top of a magnetic mask line width at distances corresponding to 1.5, 3.5 and 7.5 times the linewidth of the pattern on the mask. FIG. 8b is a graph showing the sites having a magnetic field with the strongest intensity at distances corresponding to 1.5, 3.5 and 7.5 times the linewidth of the pattern on the mask.

It clearly demonstrates an interesting property of the technique of the present invention: when the substrate is relatively far away from the mask, the magnetic field on the substrate weakens; however, it peaks in the center of the line on the mask and therefore can induce adsorption of nanoparticles with patterns much narrower than the patterns on the mask. It should be noted that the line width obtained is quite uniform. Its uniformity depends on the size of the NPs, since when NPs are smaller, the line that can be obtained is much more uniform. However, smaller NPs have a smaller magnetic dipole and therefore require a higher permanent magnetic field. For 10-nm diameter particles and since three particles define the linewidth, the width of the 30-nm lines has fluctuatuons of ±30%.

Figure 9:
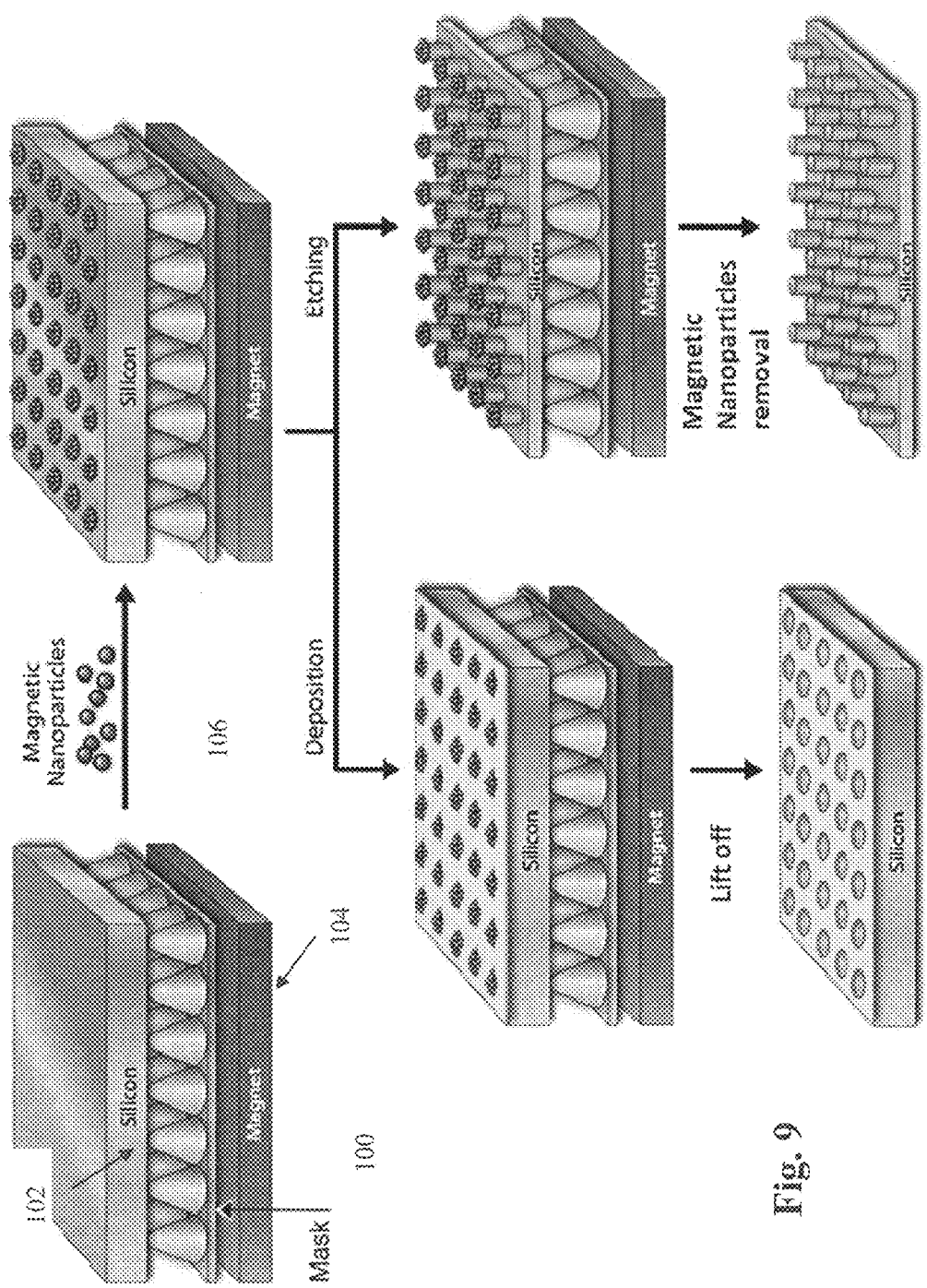
FIG. 9 is a schematic representation of the ML method of the present invention including etching and deposition processes.

Reference is made to FIG. 9 illustrating a specific but non-limiting example of the ML method including etching and deposition steps. A magnetic field is patterned on top of a substrate 102 by using a permanent magnet 104 that produces a constant field of about 100 Gauss above the substrate. A mask 100 made from paramagnetic patterns is placed between the magnet and the substrate at the back of the substrate. The mask can be either a flat surface on which paramagnetic metals are patterned by conventional photolithography or a patterned three-dimensional structure fully coated with paramagnetic metal. In the latter, the shape of the substrate defines the magnetic field on the mask. The entire assembled system (magnetic, mask, and wafer) is exposed to a solution containing magnetic nanoparticles 106. The nanoparticles 106 assemble on the substrate 102 according to the strength of the gradient in the field. The system is then placed either in an etcher or in an evaporator and the substrate is processed. The nanoparticles 106 are then removed.

For deposition and etching, the masks were prepared either using photolithography when the mask is patterned with paramagnetic metal, or using a three-dimensional non-planar mask of a silicon wafer as illustrated in the figure. In the latter case, the silicon tips array was fabricated using photolithography and sequential ion plasma etching as described in WO2009/113063 incorporated herein by reference, after which a paramagnetic metal cobalt layer was evaporated on the entire mask. By using non-planar masks, it is possible to obtain high density of high-resolution patterns, since the sharp non-planar features induce a strong magnetic field at certain spots.

In this specific and non-limiting example, the mask(s) was held at the backside of a thin silicon substrate (300 μm thick). A permanent magnet was clamped to the backside of the mask 100 to create an average field of about 100 Gauss on the silicon surface 102. The silicon substrate 102 was then exposed to a solution of 10 μg ml$^{-1}$ Fe$_3$O$_4$ NPs (10 nm diameter) 106 stabilized in aqueous solution. The concentration of NPs and the time the wafer is immersed in the solution define the resolution and uniformity of the features obtained following the etching or deposition.

In the case of the etching, the silicon substrate 102 was placed in an ion plasma etcher, ICP-RIE, and etched for 15 sec by SF$_6$ gas, using the magnetite NPs 106 as the etching mask, instead of the commonly used photoresist. After the etching process was completed, the silicon substrate 102 was washed and sonicated with hot ethanol for 10 min, then rinsed with water and dried by nitrogen stream.

Figures 10A, 10B, 10C, 10D:
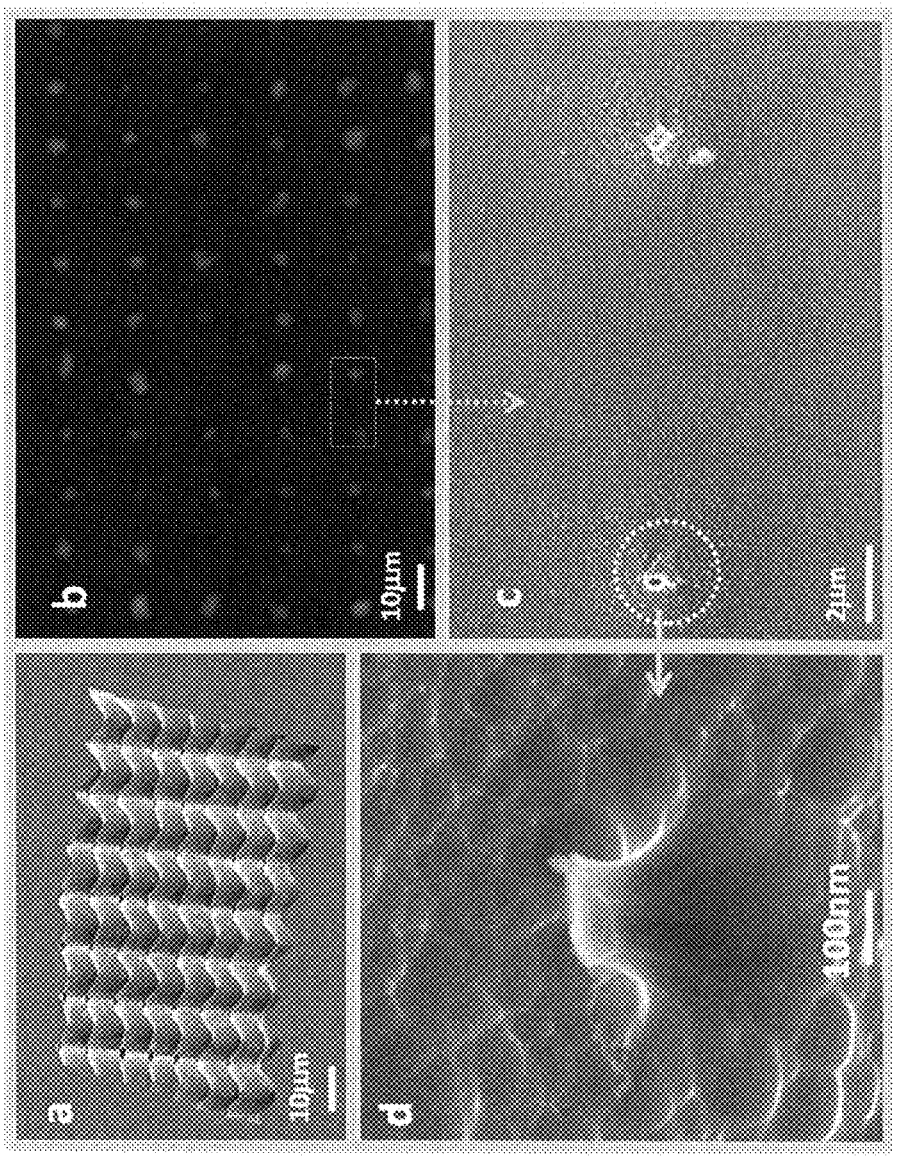
FIG. 10a is a Scanning electron microscope (SEM) image of a three-dimensional mask completely covered with a 100 nm thick layer of cobalt used for etching.
FIGS. 10b-10d are SEM images of the patterns obtained by the etching process as seen with various magnifications.

Reference is made to FIG. 10a showing scanning electron microscope (SEM) images of a mask, and FIGS. 10b-10d illustrate the patterning of silicon pillars with about a 100 nm diameter and 100 nm height obtained by etching the substrate, as seen at various magnifications (10 μm, 2 μm, 100 nm. The mask used in this process is non-planar and is produced by coating a three-dimensional patterned silicon wafer having a 100 nm thick cobalt layer.

Figures 11A, 11B, 11C:
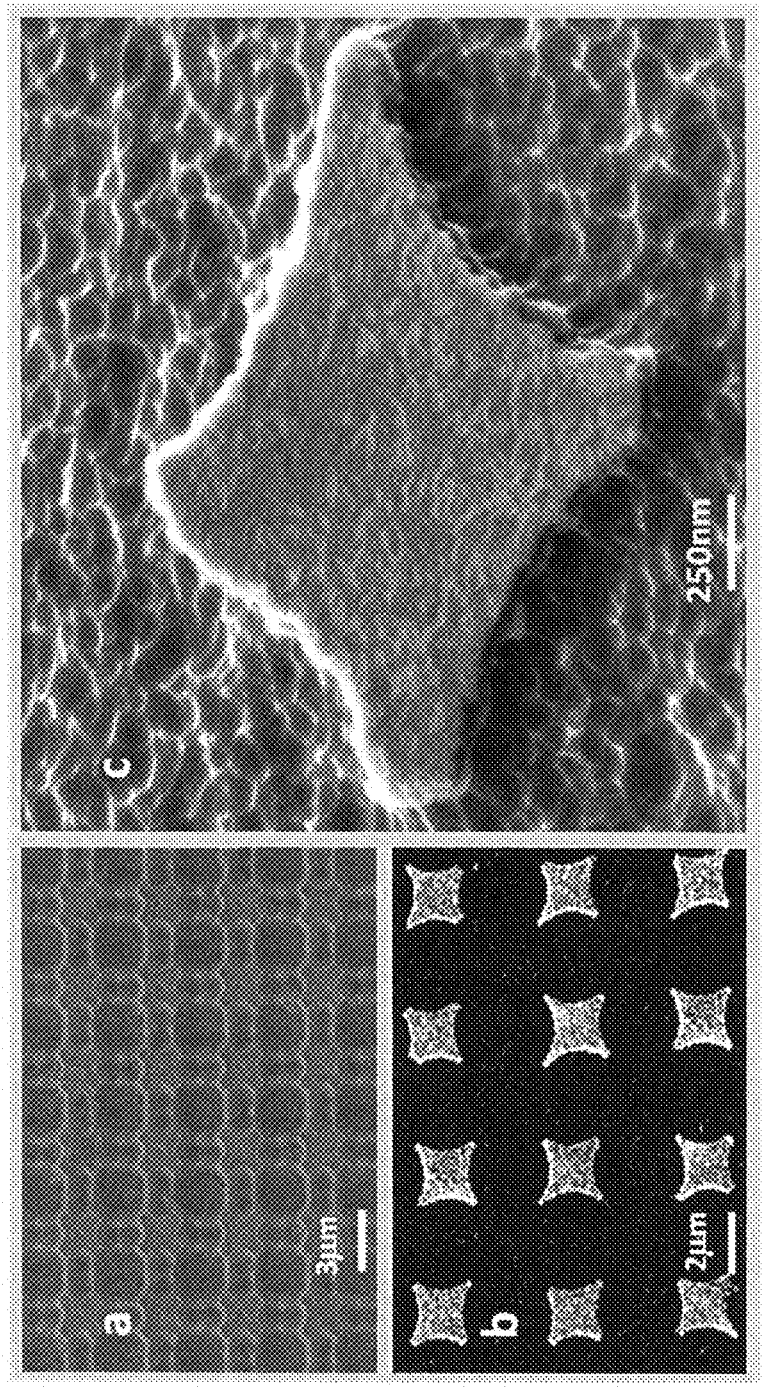
FIG. 11a is a SEM image of a flat mask in which a paramagnetic 10-nm thick layer of cobalt lines is used to define the magnetic field distribution.
FIGS. 11b-11c are SEM images of the patterns obtained by the etching process, as seen with various magnifications.

FIG. 11a illustrates a different mask based on 100 nm thick cobalt lines deposited on a flat silicon wafer. In FIGS. 11b-11c, the etched patterns are shown at two different magnifications (2 μm, 250 nm). The results shown both in FIGS. 10b-10d and 11b-11c were obtained without optimizing the process and therefore the uniformity of the structure is not ideal. However, even under these conditions clear structures are obtained. As explained above, it should be noted that not like in the conventional photolithography, in the ML technique of the present invention, the structures obtained are not identical to those on the mask. The technique is sensitive to the shape of the magnetic field on the substrate produced by the patterns on the mask and not to the patterns on the mask themselves. Hence, for obtaining a specific shape of patterns on the substrate the shape of the patterns on the mask has to be simulated to produce the required patterns on the substrate.

FIGS. 12a-12d presents SEM images obtained by etching silicon after exposing the substrate to NPs by applying a magnetic field using the mask shown in FIG. 11a. The results were obtained for various concentrations of NPs in the solution when the exposure time was kept constant (5 min). Specifically, FIG. 12a illustrates the etching for a concentration of 10 mg ml$^{-1}$; FIG. 12b for a concentration of 1 mg ml$^{-1}$, FIG. 12c for a concentration of 300 μg ml$^{-1}$ and FIG. 12d for a concentration of 100 μg ml$^{-1}$.

As clearly shown, the reproducibility and uniformity of the structures can be controlled and optimized, similarly to the optimization performed in conventional photolithography.

Metal deposition was performed using the mask shown in FIG. 13a. The mask was produced by deposition of a 50 nm thick chromium layer on a three-dimensional patterned silicon substrate. When the substrate was exposed to the magnetic field produced by the permanent magnet and the mask, the magnetic NPs assembled on the silicon substrate, as shown in FIGS. 13b-13c. Following the metal deposition, a lift-off process was performed by sonication for 5 minutes in acetone. The resulting structures are shown in FIGS. 13d-13e. The structures obtained are quite uniform and reproducible.

It should be noted that the NPs tend to assemble in multilayer structures. It should be understood that if the NPs assembled on the substrate would form a single layer, it would not be possible to fully cover the surface and spaced-apart empty regions would remain in the layer causing severe non-uniformity of the process. The multilayer structures results from the magnetic field induced by the first group of NPs that start to assemble at the high-gradient magnetic field regions on the substrate. The multilayer clusters ensure the opaque of the NPs patterns and hence contribute to the uniformity of the masking. The force applied on the magnetic NPs is given by:

$$F = \Delta \chi V (\nabla \cdot B) B \mu_0^{-1}, \quad (1)$$

where B is the flux density (Tessla), $\Delta \chi$ is the difference in susceptibility between an object and its surroundings ($10^3$-$10^5$ m$^{-3}$ for paramagnetic materials in air), V is the volume (~$1\times10^{-19}$ cm$^3$ for a 10 nm diameter particle), and $\mu_0$ is the vacuum permeability constant.

The average magnetic field applied on the substrate is about $10^{-2}$ Tessla. Decreasing the size of the patterns, for example the width of a line, while keeping good uniformity, requires using smaller particles, for example 2 nm particles. This size of particles allows achieving line widths of about 20±3 nm. Assuming that the magnetic dipole of the NPs is proportional to its volume and that the gradient of the field will increase proportionally with the field, then the magnetic field required for working with 2 nm particles is about 0.1 Tessla.

In other embodiments, the magnetic pattern generator is based on the principles of hard disk devices used in computers, and enables to obtain electronically a magnetic field spatial pattern by changing the magnetic direction using a magnetic head.

Figure 14A:
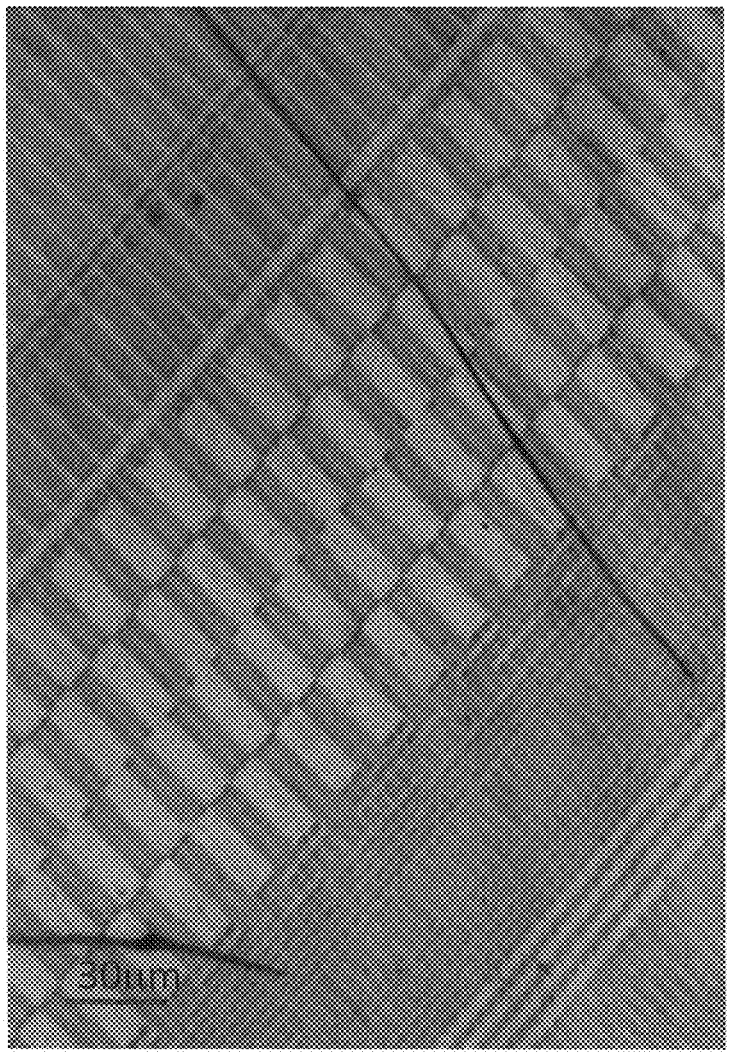
FIGS. 14a-14d are images illustrating the use of an hard disk medium as a magnetic pattern generator; in particular
Figure 14B:
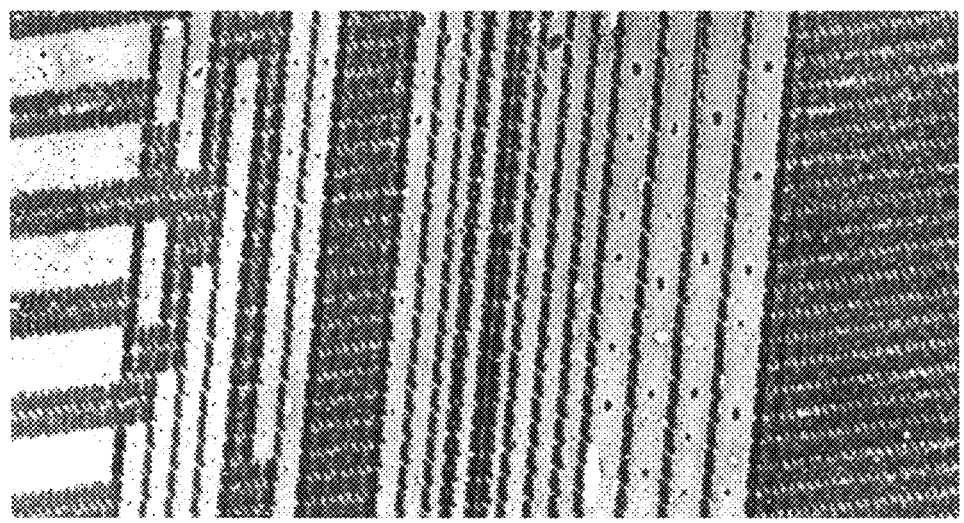
Figure 14C:
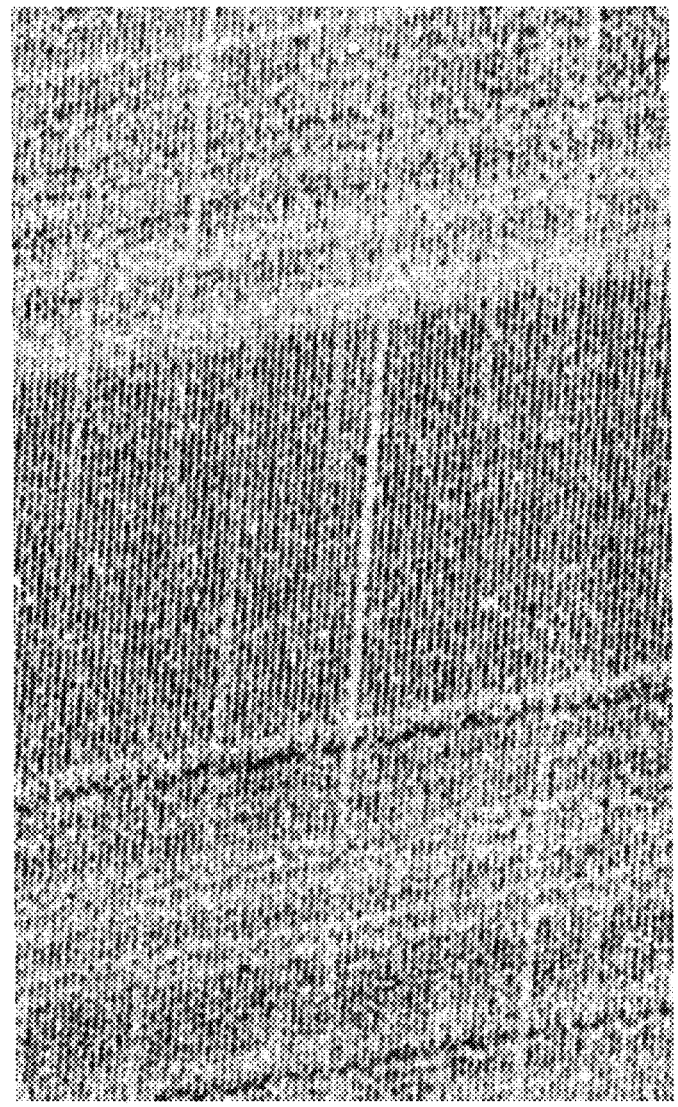
Figure 14D:
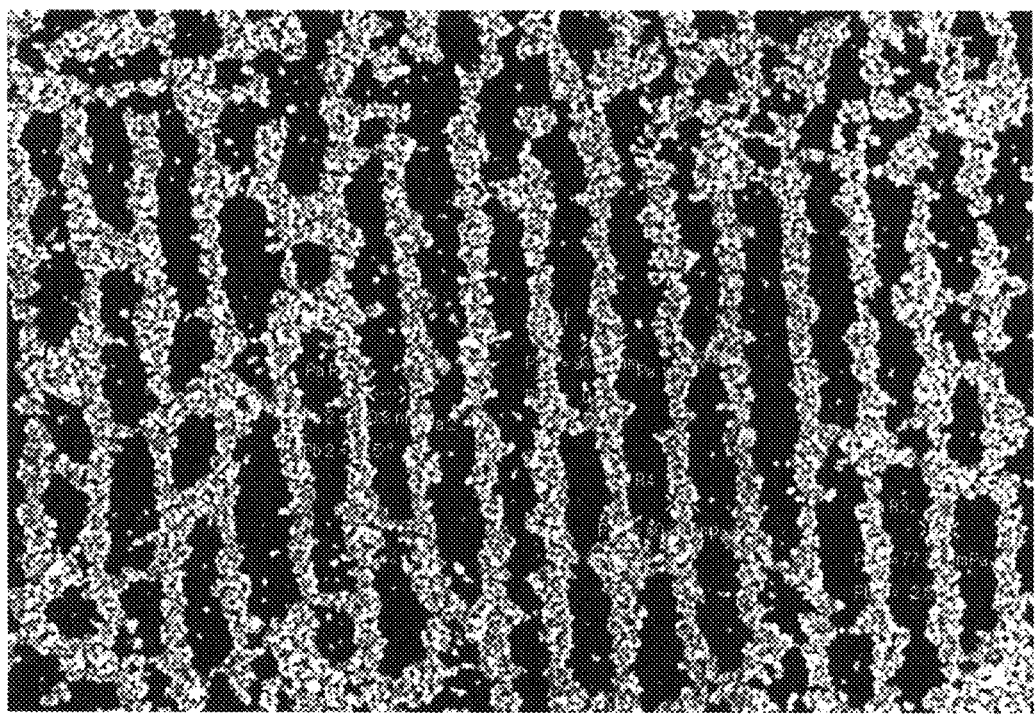

In this connection, reference is made to FIGS. 14a-14d the use of a hard disk medium as a magnetic pattern generator. FIG. 14a is a light microscope image of a pattern onto a gold substrate made by using a hard disk medium as a magnetic pattern generator and. A magnetic head, similar to that existing in hard disks devices, is used to electronically pattern the magnetic field onto a magnetic medium, in particular onto a hard disk medium. This is can be done by using a software translating a pattern (e.g. drawing patterned on the computer's screen) to magnetic shapes onto the magnetic medium e.g. the hard disk medium. The hard disk medium is then taken out from the hard-disk drive and used as a magnetic pattern generator. A thin metal or polymer film may be then deposited on top of the patterned hard-disk medium. Magnetic nanoparticles may then be used to cover the thin film applying either the negative or positive Magneto Lithography approach according to the teachings of the present invention, when the hard-disk medium is used as a magnetic pattern generator. After the patterning of the thin film, the film is taken off, and the hard disk can be reused. FIG. 14b is a SEM image of the same pattern onto a gold substrate at a higher resolution (20 μm); FIGS. 14c-14d are SEM images of the same with high resolution patterning (2 μm and 20 nm).

Figure 15A:
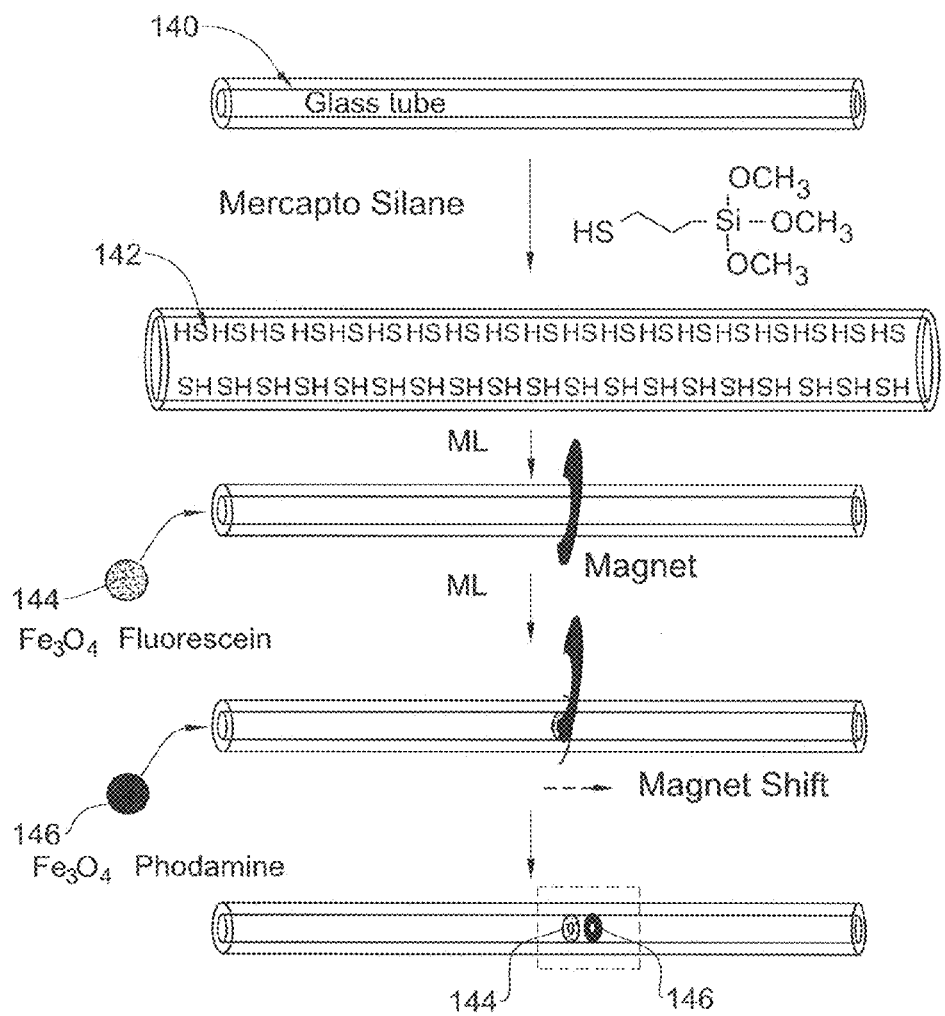
FIG. 15a is a flow chart describing the patterning of an inner tube surface by applying positive ML according to the teachings of the present invention.
Figure 15B:
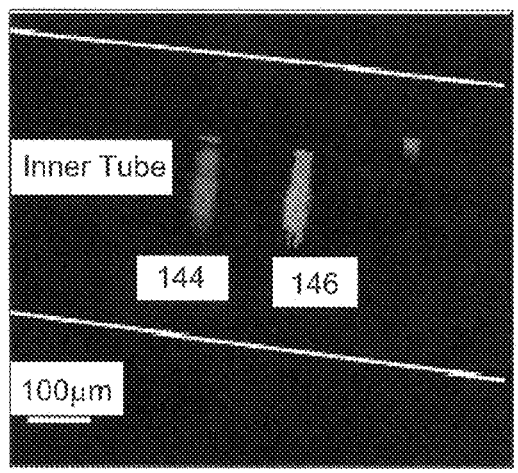

Reference is made to FIG. 15a is a flow chart describing the patterning of an inner tube surface by applying a positive ML according to the teachings of the present invention. In this specific and non-limiting example, the inner tube surface is a 200 μm diameter glass tube 140 which was immersed in bicyclohexyl (BCH) solution and was functionalized by mercapto propyl trimethoxy silane 142 (e.g. 10 mM mercapto propyl trimethoxy silan for 4 hours at room temperature). Ten-nm diameter magnetic NPs (Fe$_3$O$_4$) were coated by fluorescein 144 and sulforhodamine 146. The NPs were separated from the fluorophore solution by a magnetic field and then they were diluted in ethanol. A magnetic field (e.g. of about 100 Gauss) was applied on the tube 140 by using a permanent magnet. The fluorescein-labeled magnetic NPs 144 were injected into the tube and adsorbed at the sites at which the magnetic field gradient was maximum. After half an hour, the tube was washed with ethanol and the magnetic field was shifted to another site. Next, sulforhodamine-labeled magnetic NPs 146 were injected into the tube and they concentrated at the new site. After half an hour, the tube was washed with ethanol and dried with nitrogen. This process resulted fluorescence of both the fluorescein and sulforhodamine observed from two bands of the nanoparticles adsorbed within the patterned tube, as shown in FIG. 15b.

Figure 16A:
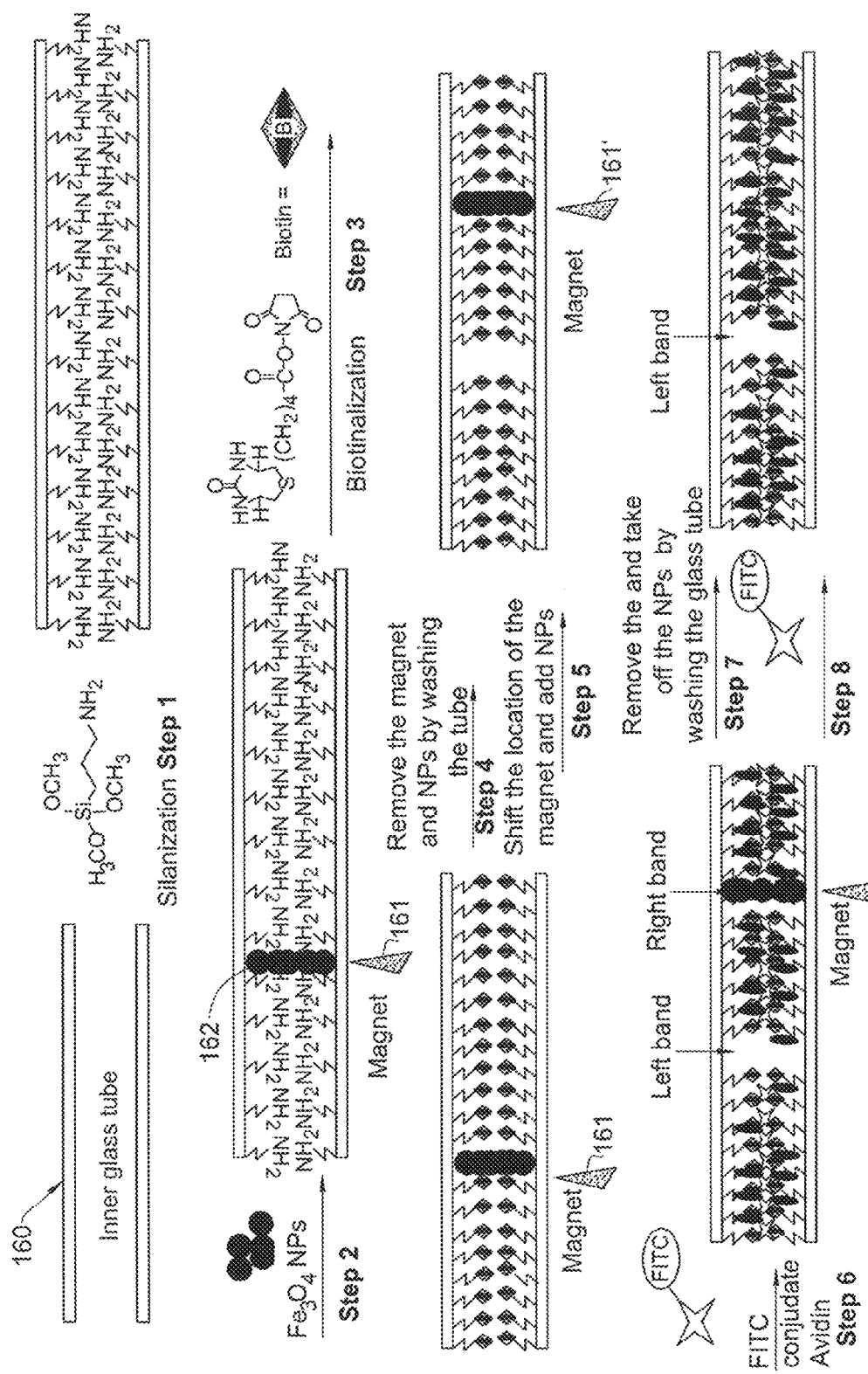
FIG. 16a is a flow chart describing the stepwise surface patterning of an inner surface of a tube by applying negative ML according to the teachings of the present invention.

FIG. 16a is a flow chart of describing the patterning of an inner tube surface by applying negative ML according to the teachings of the present invention. The inner part of a glass tube 160 (e.g. 200 μm diameter) was functionalized by amino propyl trimethoxy silane (step 1) (e.g. the tube was immersed in methanol solution with 10 mM amino propyl trimethoxy silane for 4 hours at room temperature); then a magnetic field 161 (of about 100 Gauss) was applied at one site along the tube and a solution containing Fe$_3$O$_4$ NPs 162 (e.g. of 1 mg ml$^{-1}$ Fe$_3$O$_4$ NPs) was injected into the tube (step 2). The NPs 162 are arranged as a ring at the site at which the magnetic field 161 is applied. In the next step, a solution of N-hydroxy-succinimide-biotin (NHS-biotin) e.g. of 1 mg ml$^{-1}$ NHS-biotin was reacted with the amino functional patterned surface e.g. for 1 hour. The site covered with the NPs 162 is protected and therefore does not react with the NHS-biotin (step 3). This process results in selective locations for biotinylation at the surface, at the sites which were not covered with the NPs. Since the magnetic NPs are inert to the surface, they can be removed by washing the surface after the magnetic mask is removed (step 4). In order to demonstrate the success of the method in multiple stages of patterning of the inner surface of the tube, the prepared biotinylated tube was exposed to a magnetic field 161' at a second location. NPs 162 were injected into the tube (step 5). The substrate was then exposed to a buffer phosphate solution (pH 8) e.g. a 50-mM buffer phosphate solution of fluorophore-labeled avidin (Av-FITC) e.g. 5 μg·100 μl$^{-1}$ Av-FITC (step 6). Again, the magnetic NPs were attracted by the magnetic field and assembled at the new site. Hence, the biotin groups underneath the NPs were protected and did not interact with the Av-FITC.

Figure 16B:
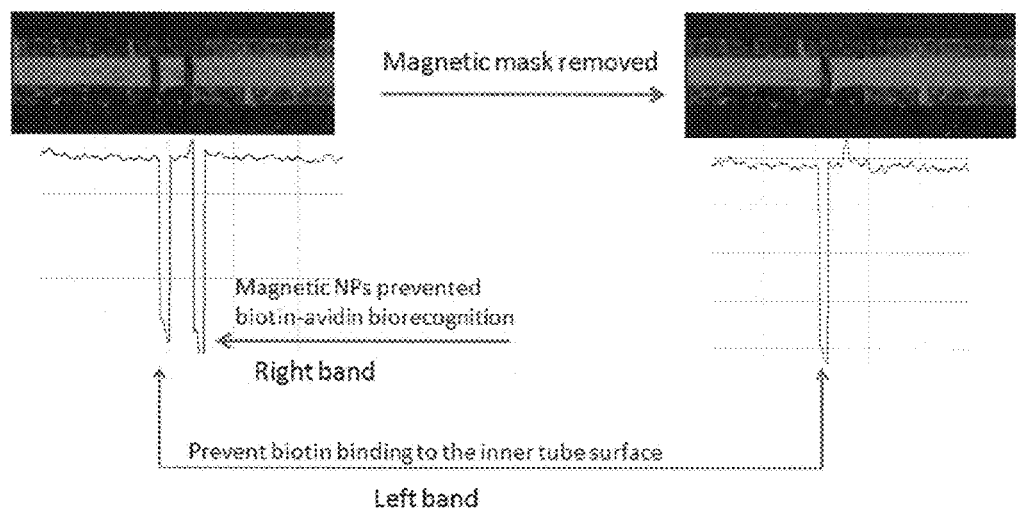

This negative ML process resulted in a patterned surface with two bands as illustrated in FIG. 16b. The left band represents the negative ML, where a reaction between biotin-NSH molecules and the amine group in the inner tube surface is prevented, whereas the right band results from NPs that prevented the interaction between the already adsorbed biotin molecules and Av-FITC in the solution. The second negative ML process is reversible, since removing the magnet causes the magnetic NPs to be released (step 7). Consequently, the biotin groups at these sites are deprotected and the Av-FITC molecules that are injected into the tube can interact with the adsorbed biotin groups (step 8), as shown FIG. 16*b*.

Therefore, the present invention provides the ability to pattern the inner surface of a tube with relatively small molecules. For sequential processes, the reaction between the reactant in the solution and the one adsorbed on the surface has to be localized.

Figure 17A:
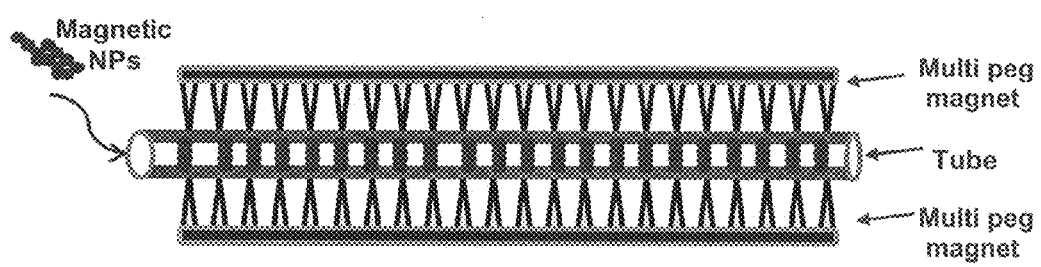
FIG. 17a is a schematic illustration describing a multi-peg magnet for applying ML in a tube.
Figure 17B:
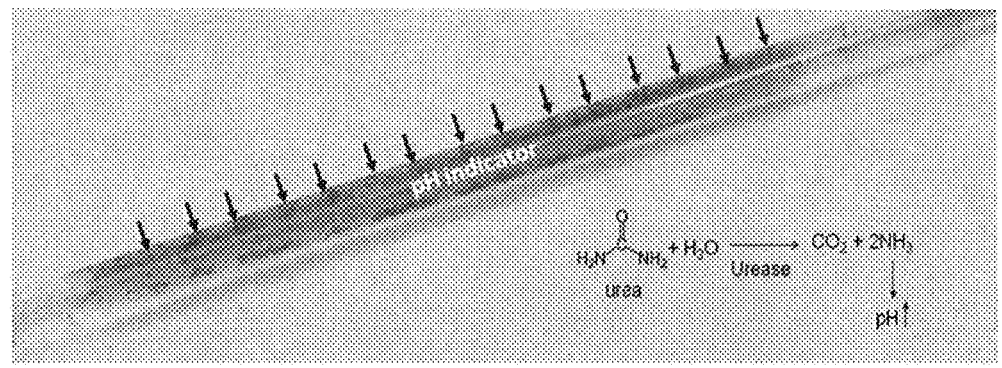
FIG. 17b shows the tube of FIG. 17a patterned with the enzyme urease by using negative ML.
Figure 17C:
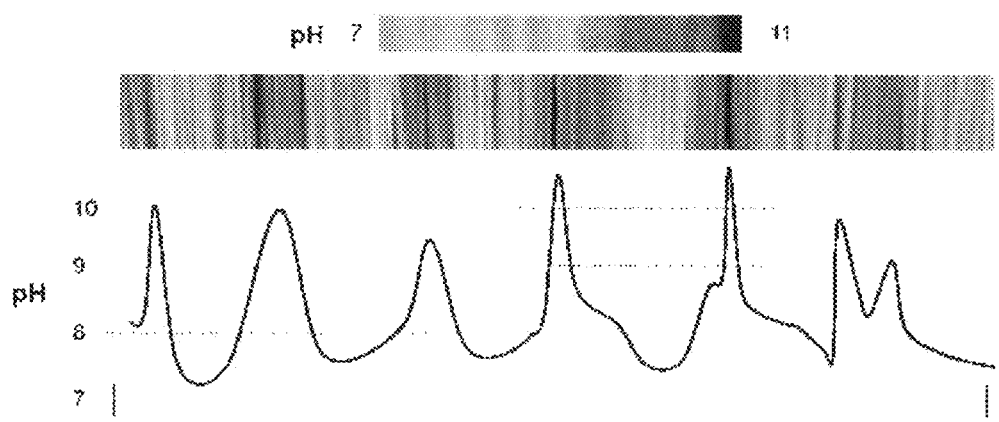
FIG. 17c shows the change in pH along the tube as obtained from the variation of the indicator's color.

The present invention also provides the ability to pattern the inner part of a tube with enzyme. In this connection, reference is made to FIGS. 17*a*-17*c* illustrating rings of enzyme urease patterned on the inside of a tube (200 μm diameter) at different places using the negative ML approach of the present invention. First, the inner surface of the tube was modified by amino propyl trimethoxy silane. The tube was immersed in methanol solution with 10 mM amino propyl trimethoxy silan for 4 hours at room temperature. Next, the tube was exposed to a multi-peg magnet (e.g. inducing a magnetic field of about 100 Gauss) and magnetic NPs (e.g. solution of 1 mg ml$^{-1}$) were injected into the tube. The magnetic NPs were arranged along the tube according to the magnetic field induced by the magnetic pegs, as shown in FIG. 17*a*. The covalent coupling of urease to the amino propyl silan was performed by injecting 0.05M HEPES buffer solution, pH 7.3, containing 0.5 mg ml$^{-1}$ urease (e.g. from jack beans, Type 3, E.C. 3.5.1.5) in the presence of 0.01 M 1-ethyl-3-(3-(dimethylamino)propyl)carbodiimide (EDC) e.g. with an incubation time of 2 h at room temperature. Consequently, the urease covalently bound to the amine groups that were not protected by the magnetic NPs. The NPs were removed by washing the tube. A solution containing urea e.g. 0.1 M urea and a pH indicator was flown/flushed through the tube. At the regions where the urease was patterned, the enzyme decomposed the urea, producing $NH_3$. As a result, the pH in that region increased and the indicator changed its color from red to green/blue at the urease binding sits. As is clearly shown in FIG. 17*b*, the high pH regions appear as spots inside the tube. The pH variation along the tube can be analyzed, based on the change in the color of the indicator, and is shown in FIG. 17*c*. This experiment proves the ability to pattern the inside of the tube with enzymes and it provides direct evidence for localizing the reaction between the enzyme and the urea.

Figure 18A:
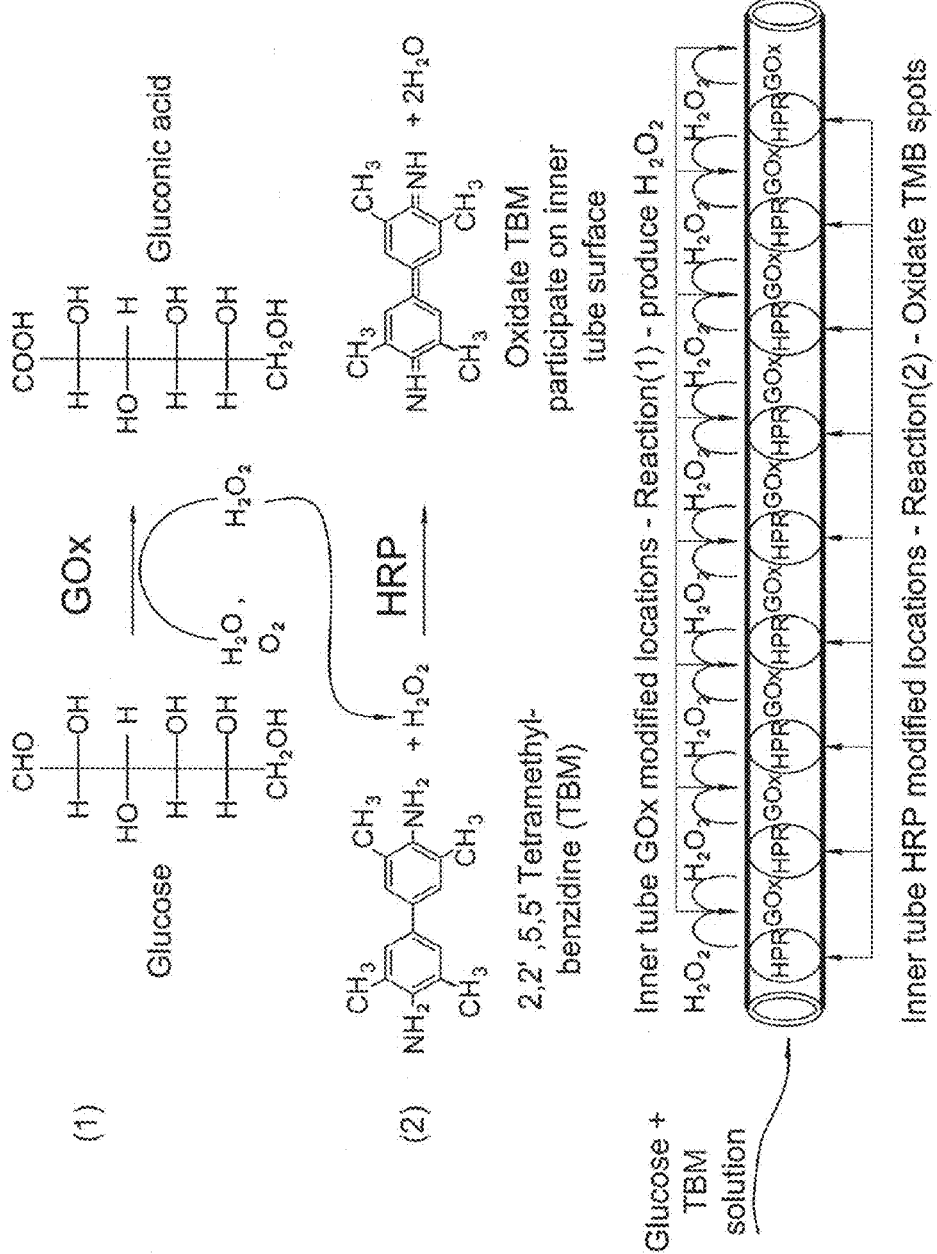
FIG. 18a is a schematic illustration of sequential enzymatic reactions inside a tube obtained by patterning proteins glucose oxidase (GOx) and horseradish peroxidase (HRP) on the inner surface of the tube.

Once the ability to have localized enzymatic reactions inside the tube was demonstrated, the negative ML of the present invention was applied for sequential enzymatic reactions. In this case, proteins glucose oxidase (GOx) and horse-radish peroxidase (HRP) were adsorbed at well-defined sites on the inner surface of a tube (e.g. 200 μm diameter tube), as shown in FIG. 18*a*. First, the inner surface of the tube was modified by amino propyl trimethoxy silane. The tube was immersed in methanol solution with 10 mM amino propyl trimethoxy silan for 4 hours at room temperature. Next, the tube was exposed to a multi-peg magnet e.g. which induced magnetic field of about 100 Gauss and magnetic NPs were injected into the tube. The magnetic NPs were arranged along the tube according to the magnetic field induced by the magnetic pegs. The covalent coupling of GOx to the amino propyl silan groups that were not protected by the magnetic NPs was performed by injecting buffer solution e.g. 0.05M HEPES buffer solution pH 7.3 containing 0.5 mg ml$^{-1}$ GOx (e.g. from *Aspergillus niger*, E.C. 1.1.3.4) in the presence of 1-ethyl-3-(3-(dimethylamino)propyl)carbodiimide (EDC) e.g. 0.01 M EDC with an incubation time of 2 h at room temperature. Consequently, the GOx covalently bound to the amine groups that were not protected by the magnetic NPs.

The NPs were removed by washing the tube. Next, a second cycle of ML was performed to protect the GOx binding sites by magnetic NPs using a multi-peg magnet that induced the magnetic field at the GOx binding sites. Then, the covalent coupling of HRP to amino propyl silane was performed by injecting buffer solution (e.g. 0.05M HEPES buffer solution) containing 0.3 mg ml$^{-1}$ HRP (RC. 1.11.1.7) in the presence of EDC (e.g. 0.01 M EDC with an incubation time of 2 h at room temperature). Consequently, the HRP covalently bound to the amine groups, which are located in-between GOx binding sites. The sequential enzymatic reaction in the tube was initiated by injecting to the tube glucose with 2,2,5,5' tetramethyl-benzidine (TMB). TMB was dissolved in ethanol then diluted with 0.1M buffer phosphate pH 6.0 with 50 mM glucose to yield the glucose solution that includes 1 mM TMB and 2%(v/v) ethanol. The glucose was oxidized by the GOx and $O_2$ to yield gluconic acid and $H_2O_2$. The $H_2O_2$ diffused to the HRP binding sites and there the HRB biocatalyzed the oxidation of TMB by $H_2O_2$, yielding an insoluble product.

Figure 18B:
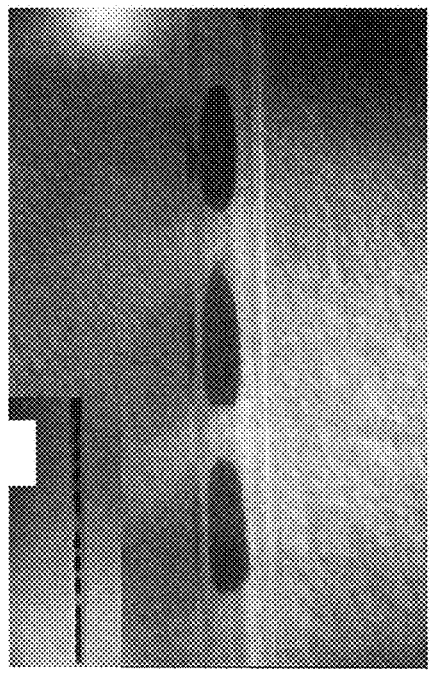
FIG. 18b is an image of the participate oxidate tetramethyl-benzidine (TMB), resulting from the sequential reaction seen as dark spots.

FIG. 18*b* shows the results of the sequential enzymatic reactions indicated by spots generated by participates of insoluble products at the location of the HRP. A set of control experiments proved that the insoluble product is generated only when all components exist, namely, when both GOx and HRP are adsorbed and glucose and TMB are dissolved in the solution.

Therefore, the present invention provides the ability to pattern the inside of a tube and to use the patterned substrate for catalyzing a reaction in a solution reactions in spatially localized regions.

The invention claimed is:

1. A method for patterning a substrate, the method comprising:
    providing a magnetic field source outside said substrate configured to create a first constant magnetic field in a magnetic field region;
    providing a patterned mask placed at a predetermined distance and spaced from a surface of said substrate in said magnetic field region, said patterned mask being separate from the substrate and configured to create regions of different magnetic properties of the magnetic field on said surface according to a desired pattern, thereby forming a modulated magnetic field along said surface;
    operating the magnetic field source thereby applying said modulated magnetic field to said surface of the substrate thus creating a certain pattern of regions of interaction to be obtained on said surface of the substrate; said desired pattern corresponds to said certain pattern for a predetermined magnetic field profile and at said predetermined distance;
    interacting said substrate with magnetic particles, while under the application of said modulated magnetic field, the magnetic particles being attracted to selected regions of interaction defined by said certain pattern while being substantially not attracted to regions outside said regions of interaction, and creating on said surface of said substrate said certain pattern of regions interacted with the magnetic particles.

2. The method of claim 1, wherein the magnetic particles are ferromagnetic nanoparticles.

3. The method of claim 1, comprising removing the magnetic particles by removing an effect of the magnetic field.

4. The method of claim 1, wherein the pattern of regions interacted with the magnetic particles is formed on the substrate using a positive lithography.

5. The method of claim 4, wherein said magnetic particles interact with the substrate via at least one of chemical recognition and biological recognition with said substrate.

6. The method of claim 1, wherein the pattern of regions interacted with the magnet particles is formed on the substrate using a negative lithography.

7. The method of claim 6, wherein said magnetic particles are inert to said substrate, blocking said selected regions of interaction on said substrate from reacting with a reacting agent.

8. The method of claim 6, further comprising interacting a reacting agent with said substrate; said magnetic particles blocking the binding of said reacting agent to said substrate, and removing the magnetic particles by removing the effect of the magnetic field, creating a negative patterned substrate.

9. The method of claim 8, wherein said magnetic particles are removed by physically displacing away the mask.

10. The method of claim 6, comprising interacting a first reacting agent with said substrate via chemical recognition and/or biological recognition at regions outside said regions of interaction; interacting said substrate partially covered by said first reacting agent with magnetic particles being attracted at said selected regions of interaction; interacting a second reacting agent with said substrate partially covered by said first reacting agent; said magnetic particles blocking the recognition between the first and second reacting agents with respect to one another, and removing the magnetic particles creating a negative patterned substrate.

11. The method of claim 10, wherein said first reacting agent comprises catalyst, creating patterned regions of said catalyst to thereby use the patterned substrate for catalyzing at least one chemical reaction in spatially localized regions.

12. The method of claim 11, wherein said catalyst includes enzymes such that said chemical reaction is an enzymatic reaction.

13. The method of claim 10, wherein said first reacting agent includes a first enzyme and said second reacting agent includes a second enzyme to thereby induce sequential enzymatic reactions.

14. The method of claim 1, comprising providing a second magnetic pattern generator being configured and operable to provide a magnetic varying properties of a magnetic field applied thereon according to a second desired pattern; applying a magnetic field to the vicinity of the substrate with said certain pattern through said second magnetic pattern generator thus creating a second pattern of magnetic field on said surface of said substrate; and interacting magnetic particles with the substrate, while under the application of the magnetic field, the particles being attracted at second selected regions of interaction defined by said second desired magnetic pattern, creating a second pattern of spaced-apart regions interacted with the particles on said surface of said substrate with said certain pattern.

15. The method of claim 1, comprising immersing the substrate in a solution; said solution containing at least one of the following: magnetic particles, and one or more reacting agents.

16. The method of claim 15, wherein the reacting agent comprises bio-molecules.

17. The method of claim 1, wherein said substrate is functionalized with a self-assembled monolayer.

18. The method of claim 1, wherein said substrate has a non-planar surface.

19. The method of claim 18, wherein said substrate is a tube and said surface is an inner surface of the tube, the particles being attracted at selected regions of interaction on the inner surface of the tube defined by said desired pattern thus creating in the inner surface of said substrate a pattern of regions interacted with the particles.

20. The method of claim 1, comprising applying said magnetic field sequentially to successive regions of said substrate.

21. The method of claim 1, comprising applying a gradient of the magnetic field to the vicinity of said substrate, interacting said substrate with the magnetic particles, creating the pattern of regions interacted with a concentration-gradient of the magnetic particles corresponding to a strength of the gradient of the magnetic field.

22. The method of claim 21, wherein said pattern of regions interacted with the concentration-gradient of the magnetic particles has a characteristic dimension narrower than the corresponding characteristic dimension of said gradient of the magnetic field, such that features of the patterned substrate are smaller than features of the pattern of the magnetic field properties created by the mask.

23. The method of claim 1, comprising selecting the size of the magnetic particles and the corresponding magnetic field to obtain a uniform pattern.

24. The method of claim 22, comprising appropriately selecting duration of the application of said magnetic field and the concentration of the magnetic particles to control features and uniformity of said pattern.

* * * * *